(12) United States Patent
Felle et al.

(10) Patent No.: US 11,788,094 B2
(45) Date of Patent: Oct. 17, 2023

(54) METHOD OF INCREASING CATALASE EXPRESSION OR ACTIVITY

(71) Applicant: BASF SE, Ludwigshafen am Rhein (DE)

(72) Inventors: Max Fabian Felle, Ludwigshafen (DE); Stefan Jenewein, Ludwigshafen (DE); Kerstin Hage, Nienburg (DE); Holger Hartmann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1458 days.

(21) Appl. No.: 16/062,291

(22) PCT Filed: Dec. 8, 2016

(86) PCT No.: PCT/EP2016/080167
§ 371 (c)(1),
(2) Date: Jun. 14, 2018

(87) PCT Pub. No.: WO2017/102523
PCT Pub. Date: Jun. 22, 2017

(65) Prior Publication Data
US 2019/0112612 A1    Apr. 18, 2019

(30) Foreign Application Priority Data
Dec. 14, 2015  (EP) .................... 15199810

(51) Int. Cl.
*C12N 15/75* (2006.01)
*C12N 15/63* (2006.01)
*C12N 9/08* (2006.01)
*C12P 1/04* (2006.01)

(52) U.S. Cl.
CPC ........... *C12N 15/75* (2013.01); *C12N 9/0065* (2013.01); *C12N 15/63* (2013.01); *C12P 1/04* (2013.01); *C12Y 111/01006* (2013.01)

(58) Field of Classification Search
None
See application file for complete search history.

(56) References Cited

PUBLICATIONS

Bagyan et al. J Bacteriol. Apr. 1998; 180(8): 2057-2062 (Year: 1998).*
De Mey et al., Construction and model-based analysis of a promoter library for *E. coli*: an indispensable tool for metabolic engineering, BMC Biotechnol., 7:34 (2007).
Helmann, Compilation and analysis of Bacillus subtilis sigma A-dependent promoter sequences: evidence for extended contact between RNA polymerase and upstream promoter DNA, Nucleic Acids Res., 23(13):2351-60 (1995).
Herbig et al., Roles of metal ions and hydrogen peroxide in modulating the interaction of the Bacillus subtilis PerR peroxide regulon repressor with operator DNA, Mol. Microbiol., 41(4):849-59 (2001).
International Application No. PCT/EP2016/080167, International Preliminary Report on Patentability, dated Jun. 19, 2018.
International Application No. PCT/EP2016/080167, International Search Report and Written Opinion, dated Mar. 3, 2017.
Jarmer et al., Sigma A recognition sites in the Bacillus subtilis genome, Microbiology, 147(Pt. 9):2417-24 (2001).
Yeh et al., The reduction in s-promoter recognition flexibility as induced by core RNAP is required for s to discern the optimal promoter spacing, Biochem. J., 455(2):185-93 (2013).
Yuzenkova et al., A new basal promoter element recognized by RNA polymerase core enzyme, EMBO J., 30(18):3766-75 (2011).

* cited by examiner

*Primary Examiner* — Christian L Fronda
(74) *Attorney, Agent, or Firm* — MARSHALL, GERSTEIN & BORUN LLP

(57) ABSTRACT

The present invention generally relates to the field of fermentation technology and microorganisms useful for such fermentations. The invention also relates to materials including nucleic acids and proteins useful for altering fermentation characteristics of microorganisms, and to microorganisms comprising such nucleic acids and/or proteins.

6 Claims, 7 Drawing Sheets
Specification includes a Sequence Listing.

Figure 5

```
                  10        20        30        40        50        60
SEQ ID NO. 1   ATTCAGCATTATCATGATCAAATCAACGATAATAAATTTTTCTTTATAATAATTATAAATAAATA
SEQ ID NO. 56  ..............................................................
SEQ ID NO. 57  ..............................................................
SEQ ID NO. 58  ..............................................................
SEQ ID NO. 59  ..............................................................
SEQ ID NO. 60  ..............................................................
SEQ ID NO. 61  ..............................................................
SEQ ID NO. 62  ..............................................................
SEQ ID NO. 63  ..............................................................
SEQ ID NO. 64  ..............................................................
SEQ ID NO. 65  ..............................................................
SEQ ID NO. 66  ..............................................................
SEQ ID NO. 67  ..............................................................
SEQ ID NO. 68  ..............................................................
SEQ ID NO. 69  ..............................................................
SEQ ID NO. 70  ..............................................................
SEQ ID NO. 71  ..............................................................

70        80        90       100
SEQ ID NO. 1   TTGTTTT-TTTCTTGAG-AAATGTTATCATTGTTTTG
SEQ ID NO. 56  .......T........-....................
SEQ ID NO. 57  .......T........-....................
SEQ ID NO. 58  ...ACA.T........-....................
SEQ ID NO. 59  ...ACA.T........-....................
SEQ ID NO. 60  .......T......TC-.......A............
SEQ ID NO. 61  .......T......TC-.......A............
SEQ ID NO. 62  ...ACA.T......TC-.......A............
SEQ ID NO. 63  ...ACA.T......TC-.......A............
SEQ ID NO. 64  .......T.G.T....-.......A............
SEQ ID NO. 65  ...ACA.T.G.T....-.......A............
SEQ ID NO. 66  ...ACA.T.G.T....-.......A............
SEQ ID NO. 67  .......T.G.T....-.......A............
SEQ ID NO. 68  .......-........A.......A............
SEQ ID NO. 69  ...ACA.-........A.......A............
SEQ ID NO. 70  ...ACA.-........A.......A............
SEQ ID NO. 71  ...ACA.-........A.......A............
```

Figure 6A

```
                  10         20         30         40         50         60         70
SEQ ID NO. 2      TCTTCTTCCTTCCTTTATTTGTAATTAACAATAATTTATCCCAATCCAGAAAAGTTATTCAGCATTTATCA
SEQ ID NO. 72     ......................................................................
SEQ ID NO. 73     ......................................................................
SEQ ID NO. 74     ......................................................................
SEQ ID NO. 75     ......................................................................
SEQ ID NO. 76     ......................................................................
SEQ ID NO. 77     ......................................................................
SEQ ID NO. 78     ......................................................................
SEQ ID NO. 79     ......................................................................
SEQ ID NO. 80     ......................................................................
SEQ ID NO. 81     ......................................................................
SEQ ID NO. 82     ......................................................................
SEQ ID NO. 83     ......................................................................
SEQ ID NO. 84     ......................................................................
SEQ ID NO. 85     ......................................................................
SEQ ID NO. 86     ......................................................................
SEQ ID NO. 87     ......................................................................

80        90        100       110       120       130
SEQ ID NO. 2      TGATCAAATCAACGATAATAAATTTTTCTTTATAATAATTATAAATATTGTTTT-TTTCTTGAG-A
SEQ ID NO. 72     ...........................................T..............-.........-.
SEQ ID NO. 73     ...........................................T..............-.........-.
SEQ ID NO. 74     ......................................................-.........-.
SEQ ID NO. 75     ......................................................-.........-.
SEQ ID NO. 76     ...........................................T....ACA.T.....-....TC-
SEQ ID NO. 77     ...........................................T....ACA.T.....-....TC-
SEQ ID NO. 78     ......................................................-.........-.
SEQ ID NO. 79     ...........................................T....ACA.T.T.G.T-....TC-
SEQ ID NO. 80     ...........................................T....ACA.T.T.G.T-....TC-
SEQ ID NO. 81     ...........................................T....ACA.T.T.G.T-....TC-
SEQ ID NO. 82     ...........................................T....ACA.T.T.G.T-....TC-
SEQ ID NO. 83     ......................................................-.........-.A
SEQ ID NO. 84     ..................................................ACA.-.........-.A
SEQ ID NO. 85     ..................................................ACA.-.........-.A
SEQ ID NO. 86     ..................................................ACA.-.........-.A
SEQ ID NO. 87     ..................................................ACA.-.........-.A
```

Fig. 6B

```
         140       150       160       170       180
         AATGTTATCATTGTTTTGTAATTAAAATTTACGCGAGGTGATCCTTTG
SEQ ID NO. 2    ................................................
SEQ ID NO. 72   ................................................
SEQ ID NO. 73   ..........A.....................................
SEQ ID NO. 74   ................................................
SEQ ID NO. 75   ..........A.....................................
SEQ ID NO. 76   ................................................
SEQ ID NO. 77   ..........A.....................................
SEQ ID NO. 78   ................................................
SEQ ID NO. 79   ..........A.....................................
SEQ ID NO. 80   ................................................
SEQ ID NO. 81   ..........A.....................................
SEQ ID NO. 82   ..........A.....................................
SEQ ID NO. 83   ................................................
SEQ ID NO. 84   ..........A.....................................
SEQ ID NO. 85   ................................................
SEQ ID NO. 86   ..........A.....................................
SEQ ID NO. 87   ................................................
```

METHOD OF INCREASING CATALASE EXPRESSION OR ACTIVITY

This application is a National Stage application of International Application No. PCT/EP2016/080167, filed Dec. 8, 2016, which claims the benefit of European Patent Application No. 15199810.1, filed on Dec. 14, 2015.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "78056 SubSeglisting.txt", which was created on Nov. 19, 2018 and is 34,581 bytes in size. The subject matter of the Sequence Listing is incorporated herein in its entirety by reference.

FIELD OF THE INVENTION

The present invention generally relates to the field of fermentation technology and microorganisms useful for such fermentations. The invention also relates to materials including nucleic acids and proteins useful for altering fermentation characteristics of microorganisms, and to microorganisms comprising such nucleic acids and/or proteins. In particular, the invention relates to materials and methods for conferring, modifying or reducing microbial stress resistance against oxidative stress.

BACKGROUND OF THE INVENTION

The biotechnological production of substances of interest is, on an industrial scale, generally performed by cultivating a microorganism in a liquid medium, wherein said microorganism is capable of producing said substance of interest under the cultivation conditions. During such liquid fermentation, individual microorganism cells experience conditions that vary greatly and in a complex way overtime. In response to such changing conditions, microorganism cells may respond by altering gene expression, which in turn may lead to an undesirably low production of the substance of interest. There is correspondingly a need to provide microorganisms with improved resilience against unfavourable fermentation conditions, thus allowing for an increased production of a substance of interest compared to comparable microorganisms.

It has thus frequently been tried to determine stress conditions during fermentations and to modify the genetic makeup of microorganisms in order to improve their resilience against such stress conditions. Unfortunately, analysis of fermentation of conditions experienced by individual microorganism cells and their genetic reactions to such conditions is notoriously difficult. Wiegand et al. (Fermentation stage-dependent adaptations of *Bacillus licheniformis* during enzyme production; Microbial Cell Factories 2013, 12:120) have tried such analysis. However, understanding of fermentation conditions still remains largely incomplete.

While Wiegand et al. reported that no vegetative catalase (KatA) protein accumulation over time could be observed in *Bacillus licheniformis* during liquid fermentation production of a subtilisin protease, the inventors have surprisingly found that increased catalase activity improves overall fermentation characteristics e.g of *B. licheniformis* in the liquid fermentation production of e.g. proteases. This was even more surprising as, according to Wiegand et al., O2 partial pressure (pO2) is severely reduced throughout basically all stages of such fermentation. Thus, formation of hydrogen peroxide as a major stressor was not to be expected.

It was thus an object of the present invention to provide materials and methods for improving fermentations. It was also an object of the present invention to provide materials and methods for conferring, modifying or reducing microbial stress resistance against oxidative stress.

BRIEF SUMMARY OF THE INVENTION

The present invention therefore provides promoters comprising a −10 type box and a −35 type box separated from one another by a linker section, wherein each box consists of a respective nucleotide sequence with a respective score obtainable by assigning a value to each nucleotide at each position according to table 1 for the −10 type box and according to table 2 for the −35 type box, and wherein the score for the −10 type box is at least 471 and for the −35 type box is at least 159, and wherein the linker section has a length of at least 14 nucleotides and an A/T content of at least 57%.

TABLE 1

| position (5'->3' direction) | A | C | G | T |
|---|---|---|---|---|
| 1 | 0 | 0 | 0 | 100 |
| 2 | 0 | 0 | 100 | 0 |
| 3 | 28 | 6 | 30 | 36 |
| 4 | 8 | 5 | 0 | 88 |
| 5 | 94 | 0 | 2 | 5 |
| 6 | 23 | 11 | 6 | 59 |
| 7 | 73 | 5 | 6 | 16 |
| 8 | 63 | 20 | 3 | 14 |
| 9 | 2 | 2 | 2 | 95 |

TABLE 2

| position (5'->3' direction) | A | C | G | T |
|---|---|---|---|---|
| 1 | 2 | 3 | 0 | 95 |
| 2 | 6 | 3 | 2 | 89 |
| 3 | 2 | 8 | 81 | 9 |
| 4 | 63 | 16 | 3 | 19 |
| 5 | 20 | 58 | 5 | 17 |
| 6 | 53 | 8 | 11 | 28 |

The promoter of the present invention preferably is a bidirectional promoter.

The present invention also provides nucleic acids comprising a promoter according to the present invention and a prokaryotic host cell comprising said nucleic acid.

The invention also provides a fermentation method for producing a fermentation product, comprising the steps of
a) providing a prokaryotic host cell comprising a nucleic acid comprising a promoter according to the present invention operably linked to a gene coding for a fermentation product, and
b) cultivating the prokaryotic host cell under conditions allowing for the expression of said gene coding for the fermentation product.

The invention also provides a fermentation method for producing a fermentation product, comprising the steps of
a) providing a prokaryotic host cell comprising a nucleic acid comprising a promoter according to the present invention operably linked to a gene coding for a catalase, and
b) cultivating the prokaryotic host cell under conditions allowing for the expression of said gene coding for the catalase.

The invention also provides fermentation methods for producing a fermentation product, comprising the steps of
a) providing a prokaryotic host cell comprising a nucleic acid comprising a bidirectional promoter of the present invention operably linked to a gene coding for a fermentation product on one strand and simultaneously operably linked to a gene coding for a catalase on the reverse strand, and
b) cultivating the prokaryotic host under conditions allowing for the expression of said gene coding for the fermentation product and said gene coding for the catalase.

The invention also provides a method of increasing catalase expression and/or catalase activity in a prokaryotic host cell, comprising the step of operably linking a promoter according to the present invention with a gene coding for a catalase.

BRIEF DESCRIPTION OF THE DRAWINGS

FIG. 5 shows a sequence alignment of the promoter sequences SEQ ID NO. 1 (not according to the invention) and SEQ ID NO. 56-71. Only the full sequence of SEQ ID NO. 1 is indicated. For all other sequences, a dot denotes an identical nucleotide as in SEQ ID NO. 1 at the corresponding position, nucleotides differing from that of SEQ ID NO. 1 at the corresponding position are spelled out. For example, SEQ ID NO. 71 differs from SEQ ID NO. 1 by 5 nucleotides.

FIG. 6A and FIG. 6B show a sequence alignment of the promoter sequences SEQ ID NO. 2 (not according to the invention) and SEQ ID NO 72-87. Only the full sequence of SEQ ID NO. 2 is indicated. For all other sequences, a dot denotes an identical nucleotide as in SEQ ID NO. 2 at the corresponding position, nucleotides differing from that of SEQ ID NO. 2 at the corresponding position are spelled out. For example, SEQ ID NO. 87 differs from SEQ ID NO. 2 by 5 nucleotides.

DETAILED DESCRIPTION OF THE INVENTION

The present invention is particularly concerned with a promoter for a prokaryotic host cell as described hereinafter. The promoter of the present invention comprises a −10 type box and a −35 type box separated from one another by a linker section. Such general promoter structure is common for prokaryotic cells and has been analysed for example by Jarmer et al, Microbiology 2001, 2417-2424.

Figure 4:
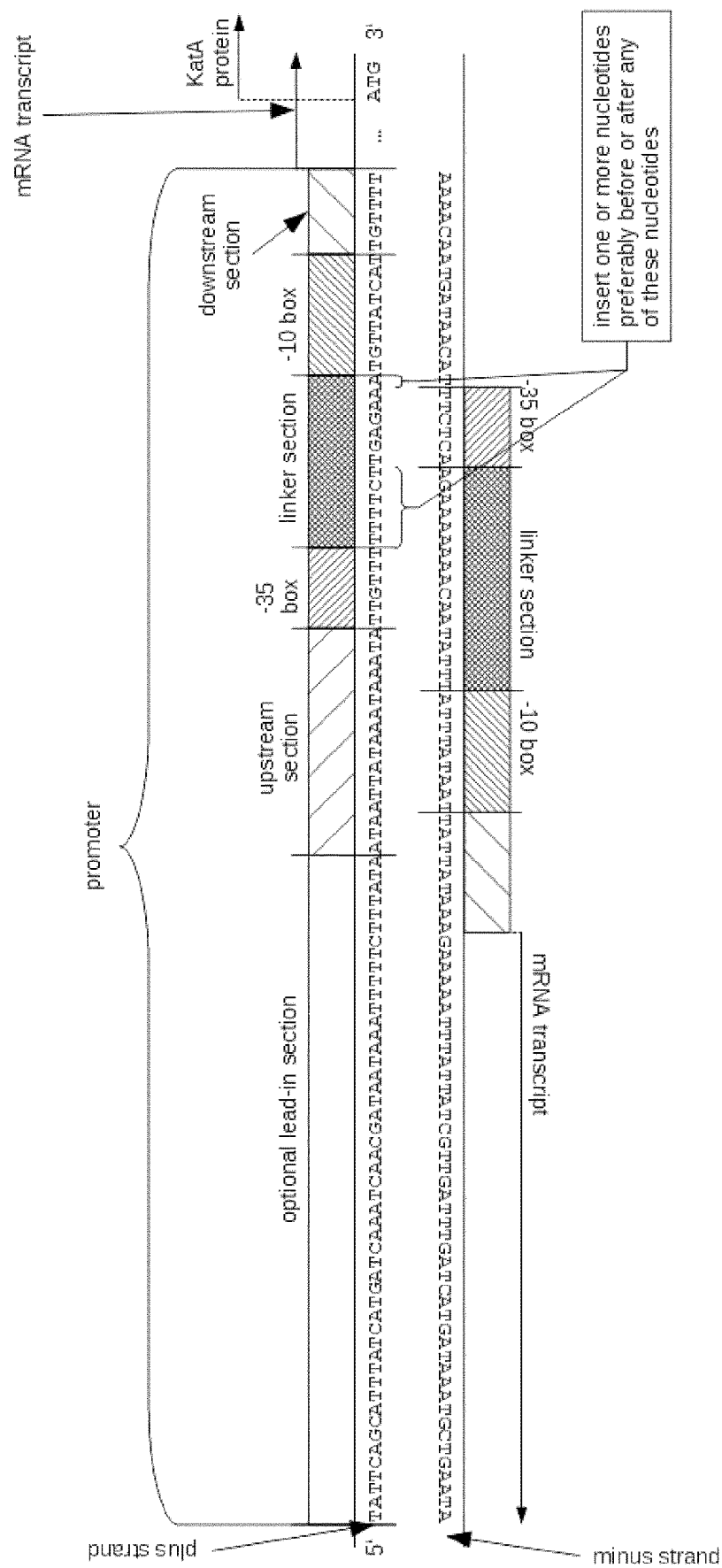
FIG. 4 shows the organization of the KatA/KatX promoters in wild-type *Bacillus licheniformis*.

By way of example, the inventors have now surprisingly found that expression of a gene operably linked to the promoter of the *Bacillus licheniformis* KatA gene can be significantly increased by altering the length of the linker section linking the −10 type box and the −35 type box of said promoter. This was particularly surprising as the promoter in *Bacillus licheniformis* overlaps with the promoter directing the expression of the KatX gene on the reverse ("minus") strand, as outlined in FIG. 4. Thus, any alteration of the KatA promoter nucleotide sequence entailed the risk of reducing or abolishing the expression of said KatX catalase, thereby potentially reducing overall catalase expression in *Bacillus licheniformis*, which would have an undesirable impact on the fermentation characteristics and particularly the yield of desired fermentation products normally obtainable by use of said *Bacillus* in a fermentation.

The promoter of the present invention generally belongs to the class of the sigma-A dependent promoters. As Jarmer et al describe, such promoters comprise two more or less conserved nucleotide sequence motifs, also called "boxes", required for initiating transcription by RNA polymerase. Even though bacterial genomes and for example the genome of *Bacillus subtilis* have been completely and repeatedly sequenced, the number of genes in such bacteria and correspondingly the number of promoters remains elusive. It is also generally not possible to reliably predict if a nucleotide sequence will be functional as a sigma-A type promoter in a given host cell. The invention provides guidance for overcoming or mitigating this unpredictability.

According to the present invention, the −10 type box and the −35 type box each consist of a respective nucleotide sequence with a respective score. The score is obtainable by assigning a value to each nucleotide at each position in 5' to 3' direction without any gaps. For the nucleotide sequence of the −10 type box, the values are chosen according to table 1, and for the −35 type box the values are chosen according to table 2. The score for the −10 type box is at least 497 and the score for the −35 type box is at least 179. Thus, the promoter of the present invention allows for a limited flexibility in view of the respective nucleotide sequences of the −10 type box and the −35 type box to account for desirable or tolerable promoter variability without generally compromising expression strength of said promoters.

The skilled person understands that the −10 type box of the promoter according to the present invention is longer than a regular −10 type box of for example *Bacillus subtilis* promoters. Such extended −10 type boxes have been described for example by Helmann for *Bacillus subtilis* promoters (Nucleic Acids Research, 1995, 2351 to 2360). However, the author had established that there is no apparent correlation between the occurrence or non-occurrence of an extended −10 type box and the length of the linker section. It was therefore surprising that by increasing the length of the linker section the expression of a gene operably linked to the promoter according to the present invention could be increased significantly. It had to be expected that the promoter on which the current invention has been first implemented will not benefit from any alteration of the length of the linker section, as this promoter, directing expression of the constitutive catalase of *Bacillus licheniformis*, is vital for survival of this microorganism under oxygen stress conditions. Thus, it had to be expected that such promoter had been optimised by evolution to its maximum expression strength. Contrary to these fears, the inventors have shown that even the promoter directing the expression of the KatA gene of *Bacillus licheniformis* benefits from the increased length of the linker section as described according to the invention.

The linker section is located adjacent to and connecting the −10 type box and the −35 type box. According to the invention, the linker section has a length of at least 14 nucleotides and an A/T content of at least 73%. A linker of such length allows to increase gene expression compared to a corresponding promoter wherein the linker section has a length of only 13 nucleotides.

Preferably, the nucleotide sequence of the linker section differs from any of the sequences SEQ ID NO. 3 to 18 by insertion of one or more thymidine and/or adenosine nucleosides before any of the nucleotide positions 1 to 5 of said respective sequences. This way, the required A/T content of the linker section can be maintained or even increased, facilitating the increase of gene expression from the promoter of the present invention. It is particularly preferred that the nucleotide sequence of the linker section differs from any of the aforementioned sequences SEQ ID NO. 3 to 18 by insertion of one or more thymidine nucleosides before any of nucleotides positions 1 to 5. Furthermore, it is preferred that the linker section does not comprise guanosine or cytidine nucleosides within the first 5 and the last 3 nucleotides of the linker section, counting in 5' to 3' direction.

Also preferably, the nucleotide sequence of the linker section differs from any of the sequences SEQ ID NO. 3 to 18 by insertion of one or more thymidine and/or adenosine nucleotides immediately before or immediately after the last nucleotide position of said respective sequences. This way, the required A/T content of the linker section also can be maintained or even increased. In cases where the promoter of the present invention is a bidirectional promoter as described herein comprising a −35 type box on the minus strand, insertion of the adenosine and/or thymidine nucleoside(s) at the end of the linker section (i.e. the "plus strand" linker section) allows to increase the length of said linker section without changing the distance of the −10 type box and −35 type box on the minus strand.

The linker section of the promoter of the present invention preferably has a length of at most 18 nucleotides. For longer linker sections, the separation between the −10 type box and the −35 type box is too large to allow for an efficient initiation of RNA transcription. Preferably, the linker section has a length of 14 to 16 nucleotides, and even more preferably has a length of 14 or 15 nucleotides. For such linker lengths, separation between the −10 type box and the −35 type box is close to optimal for initiation of RNA transcription by prokaryotic RNA polymerases of the sigma-A type. Most preferably, the linker section has a length of 14 nucleotides.

The A/T content of the linker section preferably is at least 57%, even more preferably at least 69%, even more preferably at least 71%, even more preferably at least 76%, even more preferably at least 77%, even more preferably 57% to 92%, even more preferably 69% to 92%, even more preferably 71% to 92%, even more preferably 76% to 92%, even more preferably 77% to 92%, even more preferably 85% to 92%, even more preferably 57% to 85%, even more preferably 69% to 85%, even more preferably 71% to 85%, even more preferably 76% to 85%, even more preferably 77% to 85%. Even more preferably the A/T content is 88% or, most preferably, 77%.

In a promoter according to the present invention, the nucleotide sequence of the −10 type box differs from any of the sequences SEQ ID NO. 19 to 31 by at most one nucleotide, and even more preferably is chosen from sequences SEQ ID NO. 19 to 31. Most preferably, the nucleotide sequence of the −10 type box differs by at most one nucleotide from the sequence SEQ ID NO. 19 or, even more preferably, consists of the sequence SEQ ID NO. 19. This sequence is encountered in the wild-type promoter sequence of Bacillus licheniformis KatA gene and has shown to be effective.

Accordingly, the score of the −10 type box preferably is at least 497, even more preferably at least 508, even more preferably at least 601, even more preferably at least 620, even more preferably at least 632, even more preferably at least 640, even more preferably 497 to 708, even more preferably 508 to 708, even more preferably 601 to 708, even more preferably 620 to 708, even more preferably 632 to 708, even more preferably 640 to 708, even more preferably 660 to 708, even more preferably 620 to 660, even more preferably 632 to 660, even more preferably 640 to 660. Even more preferably the score is 508 or, most preferably, 640.

Also, the nucleotide sequence of the −35 type box preferably differs from any of the sequences SEQ ID NO. 32 to 41 by at most one nucleotide and even more preferably consists of any of the sequences SEQ ID NO. 32 to 41. The sequence SEQ ID NO. 32 is encountered in the Bacillus licheniformis KatA wild-type promoter. It is thus preferred that the nucleotide sequence of the −35 type box differs from this sequence by at most one nucleotide and preferably consists of this sequence SEQ ID NO. 32.

Also, the score of the −35 type box preferably is at least 179, even more preferably at least 280, even more preferably at least 317, even more preferably at least 322, even more preferably at least 329, even more preferably 179 to 439, even more preferably 280 to 439, even more preferably 317 to 439, even more preferably 322 to 439, even more preferably 329 to 439, even more preferably 280 to 414, even more preferably 317 to 414, even more preferably 322 to 414, even more preferably 329 to 414, even more preferably 317 to 367, even more preferably 322 to 367, even more preferably 329 to 367. Even more preferably the score is 322 or, most preferably, 329.

The boundaries of promoter variability can also be expressed by the sum of scores of the −35 and −10 type box. This parameter accounts for the observation that a low-scoring −35 type box may be compensated by a higher scoring −10 type box and vice versa. The sum of scores preferably is at least 826, even more preferably at least 830, even more preferably at least 931, even more preferably at least 960, even more preferably at least 969, even more preferably 826 to 1139, even more preferably 830 to 1139, even more preferably 931 to 1139, even more preferably 960 to 1139, even more preferably 969 to 1139, even more preferably 826 to 1043, even more preferably 830 to 1043, even more preferably 931 to 1043, even more preferably 960 to 1043, even more preferably 969 to 1043, even more preferably 830 to 998, even more preferably 931 to 998, even more preferably 960 to 998, even more preferably 969 to 998, even more preferably 830 or, most preferably, 969. Where the sum of scores increases, resemblance of the promoter nucleotide sequence to that of the Bacillus licheniformis KatA wild-type promoter increases. Thus, the skilled person can be the more confident that the chosen promoter sequence will be functional and will allow to materialise the benefits of the present invention.

Correspondingly, the nucleotide sequence of the −10 type box is preferably chosen from the sequences according to SEQ ID NO. 19 to 22 and simultaneously the nucleotide sequence of the −35 type box is preferably chosen from the sequences according to SEQ ID NO. 32 to 34.

In addition to the −10 type box, the linker section and the −35 type box the promoter of the present invention preferably comprises an upstream section having a length of 20 nucleotides. The upstream section is located in 5' direction upstream of and adjacent to the −35 type box. The A/T content of the upstream section is at least 70% and the A content of the upstream region is at least 35%. Such high A/T content particularly facilitates strong expression of a gene operably linked to the promoter. Preferably, the A/T content of the upstream section is at least 77%, even more preferably at least 80%, even more preferably at least 87% and even more preferably at least 89%. Further preferably, the A/T content of the upstream region is at most 100%, less preferably the A/T content of the upstream region is at most 95% and even less preferably the A/T content is at most 90%. Correspondingly, the upstream section preferably consists of a nucleotide sequence being entirely composed of adenosine and thymidine nucleotides, less preferably the upstream section comprises one, 2 or 3 nucleotides that are not adenosine or thymidine. In the upstream section, nucleotides that are neither adenosine nor thymidine preferably are not adjacent to each other. Further preferably, the nucleotide sequence of the upstream section preferably is such that the number of nucleotides that are not consecutively repeated is at most 10 and at least 5, more preferably is at most 8 and at least 6. For example, the preferred upstream section sequence according to SEQ ID NO. 42 has 8 such isolated nucleotides at sequence position 1, 2, 5, 10, 11, 15, 19 and 20. For sequence SEQ ID NO. 55 the number would be 11 and the corresponding positions of isolated nucleotides are 1, 2, 3, 4, 7, 12, 13, 17, 18, 19 and 20. By respecting these boundaries of isolated or non-repetitive nucleotides, it is secured that the upstream section nucleotide sequence will contain approximately 5 stretches of 2 or more repeating nucleotides, of which preferably at least 4 are stretches of repeating adenosine nucleotides. Such repetitions are favourable for the binding of RNA polymerase and thus allow for a high expression of a gene operably linked to the promoter of the present invention. For the same reason, the A content of the upstream section preferably is at least 45%, even more preferably at least 52% and even more preferably is at least 60%. For the avoidance of doubt, the term "A content" for the present invention means the number of adenosine nucleotides relative to total sequence length without any gaps, that is 20 for the upstream section. Correspondingly, the term "A/T content" indicates the number of nucleotides that are either adenosine or thymidine expressed as percent of total sequence length. Preferred upstream section sequences are given herein as SEQ ID NO. 42 to 55, wherein the upstream section sequence according to SEQ ID NO. 42 is most preferred. Less preferred are such upstream sequences that differ from the sequence according to SEQ ID NO. 42 by one nucleotide. Even less preferred are sequences for the upstream section that differ from sequence SEQ ID NO. 42 by 2 nucleotides. Even less preferred are upstream sequences which differ from the sequence according to SEQ ID NO. 42 by 3 nucleotides. Particularly preferred upstream sequences are those according to any of SEQ ID NO. 43, 44, 45, 46 and 47.

It is optional but preferred that the A/T content of a sequence extending 46 nucleotides upstream ("lead-in section"), that is in 5' direction of the upstream section, is at least 70%. In the sequence according to SEQ ID NO. 2, this 46 nucleotides sequence is located from nucleotides 56 to 101.

A particularly preferred promoter according to the present invention differs from the sequence according to SEQ ID NO. 1 by at most 15 nucleotides, even more preferably at most 14 nucleotides, even more preferably at most 13 nucleotides, even more preferably at most 12 nucleotides, even more preferably at most 11 nucleotides, even more preferably at most 10 nucleotides, even more preferably at most 9 nucleotides, even more preferably at most 8 nucleotides, more preferably by at most 7 nucleotides, even more preferably by at most 6 nucleotides, even more preferably by at most 5 nucleotides, even more preferably by at most 4 nucleotides, even more preferably by at most 3 nucleotides, even more preferably by at most 2 nucleotides and even more preferably by one nucleotide, wherein in each case one such differing nucleotide is an insertion of an adenosine or thymidine nucleotide at any of positions 70 to 85, preferably at any of positions 70 to 76 according to SEQ ID NO. 1. Most preferably, the inserted nucleotide is a thymidine such that the stretch of 7 consecutive thymidine nucleotides of SEQ ID NO. 1 or 2 is extended to become a stretch of 8 thymidine nucleotides. An example of such sequence is given herein as SEQ ID NO. 56. As described below with regards to a bidirectional promoter, a nucleotide may also be inserted before or after the last nucleotide of the linker section. As indicated above, the nucleotide sequence of the −10 type box, the −35 type box and of the linker section can also vary, examples of corresponding sequences are given herein as SEQ ID NO. 57 to 71. As also indicated above, the sequence of the upstream section and the sequence extending 46 nucleotides upstream of the upstream section can also differ from the corresponding sections of sequences SEQ ID NO. 56 to 71. According to the invention, a promoter consisting of a nucleotide sequence according to SEQ ID NO. 56 is particularly preferred and described in further detail in the examples. Equally preferred is a promoter obtainable by replacing, in the sequence according to SEQ ID NO. 2, the subsequence according to SEQ ID NO. 1 by the sequence according to SEQ ID NO. 56.

The promoter of the present invention preferably is a bidirectional promoter. As described herein, a promoter controls, in the context of an mRNA transcription machinery, the binding of RNA polymerase to generally double-stranded DNA such that mRNA transcription is initiated and the sequence of a gene located downstream in 3' direction of the promoter is transcribed into an mRNA molecule of corresponding nucleotide sequence. Due to the double-strandedness of DNA, a promoter can be located on any strand of the DNA. According to the invention, the term "bidirectional promoter" is used to indicate a set of 2 promoters of overlapping nucleotide sequence, wherein one promoter controls mRNA transcription of a gene operably linked thereto on one DNA strand (also called "plus strand") and the second promoter controls expression of a second gene operably linked thereto and located on the counter strand (also called "reverse strand" or "minus strand"). Unless specifically indicated herein, all references to a promoter, a sequence, −10 type box, −35 type box, linker section, upstream section etc refer to the plus strand.

An example of a bidirectional promoter is the nucleic acid according to SEQ ID NO. 1 or SEQ ID NO. 2, which is the wild-type promoter of both KatA and KatX genes of *Bacillus licheniformis*. In these sequences, the −35 box of the promoter on the minus strand falls into the linker section on the plus strand as defined above. Thus, by increasing the length of the (plus-strand) linker section in the promoter of the present invention, the distance between the −35 type box and −10 type box on the reverse strand can also be increased. Due to the sensitivity of RNA polymerase for the distance between the −10 type box and −35 type box, it had to be expected that a change in distance between these boxes would result in a decrease of RNA transcription strength of the promoter on the minus strand. Surprisingly, however, such unwanted reduction of transcription efficiency of the minus strand promoter is not observed or at least is not unduly strong.

The minus strand promoter of a bidirectional promoter of the present invention also comprises a −10 type box, a linker section and a −35 type box. The restrictions indicated above for these elements do not necessarily apply also to the corresponding elements of the minus strand promoter. However, in preferred embodiments of the present invention the definitions and restrictions regarding the −10 type box and the −35 type box also apply to these elements of the minus strand promoter. Thus, the score of the −10 type box of the minus strand promoter preferably is at least 497, even more preferably at least 508, even more preferably 497 to 708, even more preferably 508 to 708, even more preferably 497 to 660, even more preferably 508 to 660, and the score of the −35 type box of the −strand promoter preferably is at least 179, even more preferably at least 280, even more preferably at least 317, even more preferably at least 322, even more preferably at least 329, even more preferably 179 to 439, even more preferably 280 to 439, even more preferably 317 to 439, even more preferably 322 to 439, even more preferably 280 to 414, even more preferably 317 to 414, even more preferably 322 to 414, even more preferably 317 to 367, even more preferably 322 to 367. Most preferably, the sum of scores of the −10 and −35 type box of the minus strand promoter is less than the sum of scores of the −10 and −35 type box of the plus strand promoter.

Also preferably, the −35 type box of the minus strand promoter is located within the linker section of the plus strand promoter. This way, a compact, short length bidirectional promoter is obtained with minimal interference between the plus strand promoter and the minus strand promoter and accordingly with flexibility with regards to the exact sequences of the −35 type box and −10 type box of the plus and minus strand promoter.

Preferably, the distance between the 10 type box and the −35 type box on the minus strand is not increased by increasing the length of the (plus strand) linker section. This can be achieved by inserting one or more nucleotides into the linker section "behind" the −35 box on the minus strand, for example immediately between the −10 type box and the linker section on the plus strand. This can also be achieved by deleting a number of nucleotides in the upstream section of the plus strand equal to or greater than the number of nucleotides inserted in the linker section.

The invention also provides a nucleic acid comprising a promoter of the present invention operably linked to a target gene. As indicated herein, the term "operably linked" indicates that a gene sequence is located in 3' direction of the −10 type box of the promoter such that an RNA polymerase can initiate transcription of the respective DNA strand to produce an mRNA comprising a transcript of the respective genes sequence. Typically, mRNA transcription is started in 5' direction of the start codon; the −10 type box and the start codon are thus linked by a nucleic acid preferably comprising a ribosome binding site. For the promoter of the present invention, the −10 type box described above is separated from the start codon by a nucleic acid of preferably 20 to 50 nucleotides in length. For the promoter derived from sequence SEQ ID NO. 2, the start codon can be attached immediately adjacent to the last nucleotide such that the distance between the last nucleotide of the −10 type box (ending, in sequence SEQ ID NO. 2, on " . . . caT") and the first nucleotide of the start codon is 37. Such configuration is encountered in the KatA promoter of Bacillus licheniformis as described in the examples and allows, as described in the examples, for a particularly strong expression of the KatA gene.

The nucleic acid according to the present invention thus comprises an expression cassette comprising the promoter of the present invention and operably linked thereto a target gene. In cases where the promoter of the present invention is a bidirectional promoter, the nucleic acid of the present invention preferably comprises, for each strand, one gene operably linked to the promoter of the respective strand. In such configuration the promoter of the present invention is "sandwiched" between two genes, that is one gene on either strand. This configuration allows to make full use of the benefits conferred by the promoter of the present invention and particularly allows to have both genes expressed strongly in an in a prokaryotic host cell.

The nucleic acid according to the present invention is a recombinant nucleic acid because it differs from the wild type KatA promoter of Bacillus licheniformis by the insertion of at least one nucleotide as described herein.

The target gene preferably codes for an enzyme. The enzyme preferably is selected from the group consisting of catalase, protease, amylase, carbohydrase, lipase, cellulase, pullulanase, cutinase, pectinase, mannanase, arabinase, galactanase, xylanase, oxidase, e.g. laccase, peroxidase, isomerase, transferase, kinase, and phosphatase, wherein preferred proteases are subtilisin proteases. Particularly preferred genes are genes coding for catalases, and among these the catalase genes KatA and KatX of Bacillus species, even more preferably the catalase genes coding for the KatX2 catalase of Bacillus pumilus, recorded in the Uniprot database under any of the accession numbers B4AFT4_BACPU, A8FBF9_BACP2, A0A063Z4T4_BACPU, A0A0B0Q-A43_9BACI, M5RKX5_9BACI, K2MHE7_9BACI, W8QL66_BACPU, W6ANB4_BACPU, A0A0B4S-5R6_9BACI, A0A059NBL2_9BACI, A0A0C2PYN3_BACPU and A0A081LAW9_9BACI, or coding for a catalase having at least 90% amino acid sequence identity to the KatX2 catalase recorded under any of the aforementioned Uniprot accession numbers. For the avoidance of doubt, the respective sequences are those recorded in the database on 9 Nov. 2015.

The nucleic acid according to the present invention preferably is a construct or an expression vector such that a prokaryotic host cell can be transformed with said construct or expression vector. After transformation, the nucleic acid of the present invention may be integrated into the host cell genome, for example by homologous recombination. As the result of such integration, the host cell genome comprises the target gene under the control of the promoter according to the present invention. This way a stable expression of the target gene by the host cell can be achieved even after many generations of host cell reproduction, preferably even in the absence of a selection marker like an antibiotic resistance gene.

According to the invention, the nucleic acid does not have to be integrated into the host cell genome and can instead be maintained separate therefrom. In such cases the nucleic acid according to the present invention preferably is a plasmid and comprises its own origin of replication. This way, a high copy number of the nucleic acid of the present invention can be achieved in the host cell, thus further increasing expression of the target gene or genes.

It is also possible that the nucleic acid according to the present invention is the genome of a prokaryotic host cell. As described above, this can be achieved by integrating a construct into the wild type genome of the prokaryotic host cell. Preferably, integration is such that a wild type promoter similar to the promoter of the present invention is replaced by said promoter of the present invention, preferably by homologous recombination. This way, the benefit of the present invention and particularly the increase of expression strength of the target gene compared to the corresponding wild-type can be maintained in the host cell for many generations, preferably even in the absence of a selection marker. Preferably, the promoter of the present invention replaces the wild type KatA promoter of *Bacillus licheniformis*. As described in the examples, such replacement allows to increase the expression of the catalase gene KatA without significantly compromising the expression of the KatX catalase gene and beneficially also without compromising the increase of KatX catalase expression during fermentation of *Bacillus licheniformis*.

The genome of a prokaryotic host cell can according to the invention also comprise two or more copies of the promoter of the present invention operably linked to corresponding target genes which may or may not be different for each copy of the promoter-target gene combination. This allows to maintain a high expression strength of the target genes during fermentation of the prokaryotic host cell.

The procaryotic host cell according to the present invention preferably belongs to the taxonomic class of Bacilli, preferably to order Bacillales or Lactobacillales, more preferably to a family selected from Alicyclobacillaceae, Bacillaceae, Listeriaceae, Paenibacillaceae, Pasteuriaceae, Planococcaceae, Sporolactobacillaceae, Staphylococcaceae and, Thermoactinomycetaceae, and most preferably to genus *Bacillus*. Within this genus, the procaryotic host cell of the present invention preferably belongs to species *Bacillus abyssalis, Bacillus acidiceler, Bacillus acidicola, Bacillus acidiproducens, Bacillus acidopullulyticus, Bacillus acidovorans, Bacillus aeolius, Bacillus aeris, Bacillus aerius, Bacillus aerophilus, Bacillus aestuarii, Bacillus aidingensis, Bacillus akibai, Bacillus alcaliinulinus, Bacillus alcalophilus, Bacillus algicola, Bacillus alkalinitrilicus, Bacillus alkalisediminis, Bacillus alkalitelluris, Bacillus alkalitolerans, Bacillus alkalogaya, Bacillus altitudinis, Bacillus alveayuensis, Bacillus amiliensis, Bacillus andreesenii, Bacillus aquimaris, Bacillus arbutinivorans, Bacillus aryabhattai, Bacillus asahii, Bacillus aurantiacus, Bacillus azotoformans, Bacillus badius, Bacillus baekryungensis, Bacillus bataviensis, Bacillus beijingensis, Bacillus benzoevorans, Bacillus beringensis, Bacillus berkeleyi, Bacillus beveridgei, Bacillus bogoriensis, Bacillus bombysepticus, Bacillus boroniphilus, Bacillus butanolivorans, Bacillus canaveralius, Bacillus carboniphilus, Bacillus casamancensis, Bacillus catenulatus, Bacillus cecembensis, Bacillus cellulosilyticus, Bacillus cereus* group, *Bacillus* cf. *pumilus* SG2, *Bacillus chagannorensis, Bacillus chandigarhensis, Bacillus chungangensis, Bacillus cibi, Bacillus circulans, Bacillus clausii, Bacillus coagulans, Bacillus coahuilensis, Bacillus cohnii, Bacillus composti, Bacillus coniferum, Bacillus daliensis, Bacillus danangensis, Bacillus decisifrondis, Bacillus decolorationis, Bacillus deramificans, Bacillus deserti, Bacillus djibelorensis, Bacillus drentensis, Bacillus eiseniae, Bacillus endophyticus, Bacillus endoradicis, Bacillus farraginis, Bacillus fastidiosus, Bacillus ferrariarum, Bacillus firmis, Bacillus firmus, Bacillus flavocaldarius, Bacillus flexus, Bacillus foraminis, Bacillus fordii, Bacillus fortis, Bacillus fucosivorans, Bacillus fumarioli, Bacillus funiculus, Bacillus galactosidilyticus, Bacillus galliciensis, Bacillus gibsonii, Bacillus ginsengisoli, Bacillus ginsengi, Bacillus ginsengihumi, Bacillus ginsengisoli, Bacillus gottheilii, Bacillus graminis, Bacillus granadensis, Bacillus hackensackii, Bacillus halmapalus, Bacillus halochares, Bacillus halodurans, Bacillus halosaccharovorans, Bacillus hemicellulosilyticus, Bacillus hemicentroti, Bacillus herbersteinensis, Bacillus horikoshii, Bacillus homeckiae, Bacillus horti, Bacillus humi, Bacillus hunanensis, Bacillus hwajinpoensis, Bacillus idriensis, Bacillus indicus, Bacillus infantis, Bacillus infernus, Bacillus intermedius, Bacillus iranensis, Bacillus isabeliae, Bacillus israeli, Bacillus isronensis, Bacillus jeotgali, Bacillus kochii, Bacillus koreensis, Bacillus korlensis, Bacillus kribbensis, Bacillus krulwichiae, Bacillus lehensis, Bacillus lentus, Bacillus litoralis, Bacillus locisalis, Bacillus longiquaesitum, Bacillus longisporus, Bacillus luciferensis, Bacillus luteolus, Bacillus mangrovensis, Bacillus mannanilyticus, Bacillus marcorestinctum, Bacillus marisflavi, Bacillus marmarensis, Bacillus massilioanorexius, Bacillus massiliosenegalensis, Bacillus megaterium, Bacillus meqaterium, Bacillus methanolicus, Bacillus methylotrophicus, Bacillus muralis, Bacillus murimartini, Bacillus nanhaiisediminis, Bacillus nealsonii, Bacillus neizhouensis, Bacillus nematocida, Bacillus niabensis, Bacillus niacini, Bacillus nitritophilus, Bacillus novalis, Bacillus oceanisediminis, Bacillus ohbensis, Bacillus okhensis, Bacillus okuhidensis, Bacillus oleronius, Bacillus olivae, Bacillus oryzae, Bacillus oshimensis, Bacillus pakistanensis, Bacillus panaciterrae, Bacillus patagoniensis, Bacillus persicus, Bacillus pervagus, Bacillus pichinotyi, Bacillus plakortidis, Bacillus pocheonensis, Bacillus polyfermenticus, Bacillus polygoni, Bacillus pseudalcaliphilus, Bacillus pseudofirmus, Bacillus pseudomegaterium, Bacillus pseudomycoides, Bacillus psychrosaccharolyticus, Bacillus pumilus, Bacillus purgationiresistens, Bacillus qingdaonensis, Bacillus racemilacticus, Bacillus rhizosphaerae, Bacillus ruris, Bacillus safensis, Bacillus salarius, Bacillus saliphilus, Bacillus salsus, Bacillus selenatarsenatis, Bacillus senegalensis, Bacillus seohaeanensis, Bacillus shackletonii, Bacillus shandongensis, Bacillus siamensis, Bacillus similis, Bacillus simplex, Bacillus siralis, Bacillus smithii, Bacillus soli, Bacillus songklensis, Bacillus sporothermodurans, Bacillus stratosphericus, Bacillus stratosphericusi, Bacillus subterraneus, Bacillus subtilis* group, *Bacillus taeanensis, Bacillus tequilensis, Bacillus thaonhiensis, Bacillus thermoalkalophilus, Bacillus thermoamyloliquefaciens, Bacillus thermoamylovorans, Bacillus thermocopriae, Bacillus thermolactis, Bacillus thermophilus, Bacillus thermoproteolyticus, Bacillus thermoterrestris, Bacillus thermotolerans, Bacillus thermozeamaize, Bacillus thioparans, Bacillus tianmuensis, Bacillus timonensis, Bacillus tipchiralis, Bacillus trypoxylicola, Bacillus vietnamensis, Bacillus vireti, Bacillus viscosus, Bacillus vitellinus, Bacillus wakoensis, Bacillus xiaoxiensis* or *Bacillus zhanjiangensis*, more preferably to species *Bacillus amyloliquefaciens, Bacillus brevis, Bacillus dausii, Bacillus coagulans, Bacillus licheniformis, Bacillus pumilus* or *Bacillus subtilis*, even more preferably to species *Bacillus subtilis, Bacillus licheniformis* or *Bacillus pumilus* and most preferably to species *Bacillus licheniformis*. Other preferred host cells belong to the genera *Corynebacterium, Myceliophthora* and *Basfia*, preferably to any of the species *Corynebacterium glutamicum, Myceliophthora thermophila* C1 and *Basfia succiniciproducens*.

The invention also provides fermentation methods for producing a fermentation product. The fermentation product preferably is a protein or polypeptide of at least 5 amino acids length, even more preferably at least 20 amino acids. In particular, the fermentation product can be coded for by the target gene as described above. However, the fermentation product can also be coded for by one or more genes located elsewhere and operably linked to respective promoters other than a promoter according to the present invention; such promoter-gene combinations can be located for example in the genome or in extra-genomic nucleic acids, for example on one or more plasmids, in a fermentation host cell. From an economic perspective, the value of a fermentation method according to the present invention may lie not in the very fermentation product as described before, that is the protein or polypeptide, but in a metabolite obtainable or obtained by action of said protein or polypeptide. An example of such action is the conversion of one substance to another substance, for example the generation of energy equivalents (for example ATP) by decomposition of nutrients, for example sugars, fatty acids and/or proteins. However, such metabolic processes depend on the prior formation of proteins or polypeptides and typically of enzymes. It is thus warranted for the purposes of the present invention to call these proteins or polypeptides and particularly these enzymes "fermentation product".

A preferred fermentation method according to the present invention comprises the step of providing a prokaryotic host cell comprising a nucleic acid, wherein the nucleic acid comprises a promoter according to the present invention operably linked to a gene coding for a fermentation product. Another preferred fermentation method according to the present invention comprises the step of providing a prokaryotic host cell comprising a nucleic acid which comprises, as a first promoter, a promoter according to the present invention operably linked to a gene coding for a catalase, and also comprising, on the same or another nucleic acid molecule or, in case of a bidirectional promoter, on the minus strand of the nucleic acid molecule, a second promoter operably linked to a gene coding for a fermentation product. Either preferred method further comprises the step of cultivating the prokaryotic host cell under conditions allowing for the expression of said gene coding for the fermentation product. In those cases where the prokaryotic host cell comprises a gene coding for a catalase operably linked to a promoter according to the present invention, cultivating the prokaryotic host cell also entails the cultivation under such conditions as to allow for the expression of said gene coding for the catalase. A fermentation method according to the present invention allows to make use of the benefits conferred by the promoter of the present invention, and particularly allows to produce during fermentation high amounts of the gene coding for the fermentation product (which can be, as described before, a catalase), in particular by securing a high level of expression of the gene could coding for the fermentation product. In those cases where the fermentation method makes use of a promoter according to the present invention operably linked to a catalase gene the fermentation method benefits from an increase of catalase gene expression and correspondingly of catalase activity compared to the wild type KatA promoter of *Bacillus licheniformis*. Insofar, further details are given particularly by the accompanying examples.

As described above, the promoter of the present invention preferably is a bidirectional promoter, for example according to any of sequences SEQ ID NO. 72 to 87. Describing the promoter of the present invention by way of analogy to the wild type bidirectional promoter of the KatA and KatX genes of *Bacillus licheniformis*, the present invention allows to operably linked two independent genes to the bidirectional promoter just as if the genes coding for KatA and/or KatX would be replaced. Described in the examples, expression characteristics of the gene on the "KatA side" differs from that of a gene on the "KatX side" of the promoter: the gene on the "KatA side" can be transcribed and expressed at a constitutively high level during fermentation, and the gene of the "KatX side" can have its transcription and expression increased during fermentation time to reach the expression strength of the gene on the "KatA side". Thus, by placing a gene on the minus strand relative to the sequences of the promoter of the present invention depicted herein, i.e. the "KatX side", it is possible to have this gene expressed in increasing strength during fermentation, thus effectively delaying the production of the corresponding gene product to later stages of a fermentation process. This is particularly advantageous where such gene product is susceptible to damage is over time or where formation of the gene product would undesirably reduce the growth of corresponding host cells during early stages of a fermentation process. Thus, the present invention beneficially allows to tailor gene expression according to the specific needs of a fermentation method and also in view of constraints imposed by the fermentation product in question.

The invention correspondingly also provides a fermentation method for producing a fermentation product, comprising the steps of
a) providing a prokaryotic host cell comprising a nucleic acid comprising a bidirectional promoter of the present invention operably linked to a gene coding for a fermentation product on one strand (plus strand) and simultaneously operably linked to a gene coding for a catalase on the minus strand, and
b) cultivating the prokaryotic host under conditions allowing for the expression of said gene coding for the fermentation product and said gene coding for the catalase.

This way, the fermentation process of the present invention benefits from the strong and timely expression of both genes, that is the gene coding for the fermentation product and the gene coding for the catalase. The expression of the gene coding for a catalase by the promoter of the present invention (on the plus or minus strand) beneficially increases the prokaryotic host cells resilience against oxidative stress and thereby aids in the production of the fermentation product by conferring or increasing protection against oxidation of the host cell, any of its metabolic products and/or of the fermentation product.

As described above the invention also provides a method of increasing catalase expression and/or catalase activity in a prokaryotic host cell, compared to the catalase expression and/or catalase activity, respectively, in wild type *Bacillus licheniformis*, comprising the step of operably linking a promoter according to the present invention with a gene coding for a catalase. For the avoidance of doubt, "increase of expression" biochemically means an increase of corresponding mRNA concentration compared to the wild-type KatA promoter of *Bacillus licheniformis*.

Nucleic acid sequences referred to in the context of the present invention are particularly:

| SEQ ID NO. | sequence | comment |
|---|---|---|
| SEQ ID NO. 1 | ATTCAGCATTTATCATGATCAAATCAACGATAATAAATTTTCTTTATAATAATTATAAATAAATATTGTTTTTTCTTGAGAAATGTTATCATTGTTTTG | wt promoter |
| SEQ ID NO. 2 | TCTTCTTCCTCCTTTATTTGTAATTAACAATAATTTATCCCAATCCAGAAAAGTTATTCAGCATTTATCATGATCAAATCAACGATAATAAATTTTCTTTATAATAATTATAAATAAATATTGTTTTTTTCTTGAGAAATGTTATCATTGTTTTGTAATTAAAATTTACGCGAGGTGATCCTTTG | wt promoter |
| SEQ ID NO. 3 | TTTTCTTGAGAAA | 77% A/T content wt linker |
| SEQ ID NO. 4 | TTTTCTTGTCAAA | 77% A/T content linker; minus strand comprises "TTGACA" -35 type box |
| SEQ ID NO. 5 | TTGTTTTGAGAAA | 77% A/T content linker; minus strand comprises "TTCTCA" KatX -35 type box |
| SEQ ID NO. 6 | TTTCTTGAGAAAA | 77% A/T content linker; minus strand comprises "TTCTCA" KatX -35 type box |
| SEQ ID NO. 7 | TTAGATTGACAAA | 77% A/T content linker; minus strand comprises "TTGTCA" score 395 -35 type box |
| SEQ ID NO. 8 | TTGCATTGAGAAA | 69% A/T content linker; minus strand comprises "TTCTCA" KatX -35 type box |
| SEQ ID NO. 9 | TTTGAGTGACAAA | 69% A/T content linker; minus strand comprises "TTGTCA" score 395 -35 type box |
| SEQ ID NO. 10 | TCCAAATCAAAGA | 69% A/T content linker; minus strand comprises "TTGATT" score 373 -35 type box, cf. SEQ ID NO. 36 |
| SEQ ID NO. 11 | TTGAGTGAGAAAA | 69% A/T content linker; minus strand comprises "TTCTCA" KatX -35 type box |
| SEQ ID NO. 12 | TTTTCTTGACAAG | 69% A/T content linker; minus strand comprises "TTGTCA" score 395 -35 type box |
| SEQ ID NO. 13 | TTTTGTGTAAAGG | 69% A/T content linker; minus strand comprises "TTTACA" score 367 -35 type box, cf. SEQ ID NO. 37 |
| SEQ ID NO. 14 | TTTTCTTGAAAAA | 85% A/T content linker; minus strand comprises "TTTTCA" score 323 -35 type box, cf. SEQ ID NO. 38 |
| SEQ ID NO. 15 | TTTTCTTTACAAA | 85% A/T content linker; minus strand comprises "TTGTAA" score 357 -35 type box |
| SEQ ID NO. 16 | ATTTTTTGAGAAA | 85% A/T content linker; minus strand comprises "TTCTCA" KatX -35 type box |

-continued

| SEQ ID NO. | sequence | comment |
|---|---|---|
| SEQ ID NO. 17 | TTTATGAGAATAA | 85% A/T content linker; minus strand comprises "TTCTCA" KatX -35 type box |
| SEQ ID NO. 18 | TTTTTTAAACAAA | 92% A/T content linker; minus strand comprises "TTGTTT" KatA -35 type box |
| SEQ ID NO. 19 | TGTTATCAT | 640 score KatA wt -10 type box |
| SEQ ID NO. 20 | TGTTATAAT | 708 score -10 type box |
| SEQ ID NO. 21 | TGTTATGAT | 641 score -10 type box |
| SEQ ID NO. 22 | TGATATCAT | 632 score -10 type box |
| SEQ ID NO. 23 | TGTTATTAA | 558 score -10 type box |
| SEQ ID NO. 24 | TATTATAAT | 608 score -10 type box |
| SEQ ID NO. 25 | TAATATAAT | 600 score -10 type box |
| SEQ ID NO. 26 | TATTAAAAT | 572 score -10 type box |
| SEQ ID NO. 27 | TATTATGTT | 492 score -10 type box |
| SEQ ID NO. 28 | ATTTATAAT | 508 score -10 type box |
| SEQ ID NO. 29 | ATTTAAAAT | 472 score -10 type box |
| SEQ ID NO. 30 | TTTTATTTT | 502 score -10 type box |
| SEQ ID NO. 31 | TTTTTTTAT | 462 score -10 type box |
| SEQ ID NO. 32 | TTGTTT | 329 score KatA wt -35 type box |
| SEQ ID NO. 33 | TTGACA | 439 score -35 type box |
| SEQ ID NO. 34 | TTGACT | 414 score -35 type box |
| SEQ ID NO. 35 | TTGAAA | 401 score -35 type box |
| SEQ ID NO. 36 | TTGATT | 373 score -35 type box |
| SEQ ID NO. 37 | TTTACA | 367 score -35 type box |
| SEQ ID NO. 38 | TTTTCA | 323 score -35 type box |
| SEQ ID NO. 39 | TTCTCA | 322 score -35 type box |
| SEQ ID NO. 40 | TTCATT | 300 score -35 type box |
| SEQ ID NO. 41 | TTCTTA | 281 score -35 type box |

-continued

| SEQ ID NO. | sequence | comment |
|---|---|---|
| SEQ ID NO. 42 | ATAATAATTATAAATAAATA | wt upstream box |
| SEQ ID NO. 43 | TATAATAATTATAAATAAAT | upstream box |
| SEQ ID NO. 44 | TTATAATAATTATAAATAAA | upstream box |
| SEQ ID NO. 45 | TTTATAATAATTATAAATAA | upstream box |
| SEQ ID NO. 46 | CTTTATAATAATTATAAATA | upstream box |
| SEQ ID NO. 47 | TCTTTATAATAATTATAAAT | upstream box |
| SEQ ID NO. 48 | ATAATAATTATAAATAAATC | upstream box |
| SEQ ID NO. 49 | TATAATAATTATAAATAAAC | upstream box |
| SEQ ID NO. 50 | TTATAATAATTATAAATAAC | upstream box |
| SEQ ID NO. 51 | TTTATAATAATTATAAATAC | upstream box |
| SEQ ID NO. 52 | CTTTATAATAATTATAAATC | upstream box |
| SEQ ID NO. 53 | TCTTTATAATAATTATAAAC | upstream box |
| SEQ ID NO. 54 | CATAATAATTATAAATAGAC | upstream box |
| SEQ ID NO. 55 | TCATAATAATTATAAATGAC | upstream box |
| SEQ ID NO. 56 | ATTCAGCATTTATCATGATCAAATCAACGATAATA AATTTTTCTTTATAATAATTATAAATAAATATTGTT TTTTTCTTGAGAAATGTTATCATTGTTTTG | promotor variant |
| SEQ ID NO. 57 | ATTCAGCATTTATCATGATCAAATCAACGATAATA AATTTTTCTTTATAATAATTATAAATAAATATTGTT TTTTTCTTGAGAAATGTTATAATTGTTTTG | promotor variant with SEQ ID NO. 20 |
| SEQ ID NO. 58 | ATTCAGCATTTATCATGATCAAATCAACGATAATA AATTTTTCTTTATAATAATTATAAATAAATATTGAC ATTTTTCTTGAGAAATGTTATCATTGTTTTG | promotor variant with SEQ ID NO. 33 |
| SEQ ID NO. 59 | ATTCAGCATTTATCATGATCAAATCAACGATAATA AATTTTTCTTTATAATAATTATAAATAAATATTGAC ATTTTTCTTGAGAAATGTTATAATTGTTTTG | promotor variant with SEQ ID NO. 20 and SEQ ID NO. 33 |
| SEQ ID NO. 60 | ATTCAGCATTTATCATGATCAAATCAACGATAATA AATTTTTCTTTATAATAATTATAAATAAATATTGTT TTTTTCTTGTCAAATGTTATCATTGTTTTG | promotor variant with SEQ ID NO. 4 |
| SEQ ID NO. 61 | ATTCAGCATTTATCATGATCAAATCAACGATAATA AATTTTTCTTTATAATAATTATAAATAAATATTGTT TTTTTCTTGTCAAATGTTATAATTGTTTTG | promotor variant with SEQ ID NO. 4 and SEQ ID NO. 20 |
| SEQ ID NO. 62 | ATTCAGCATTTATCATGATCAAATCAACGATAATA AATTTTTCTTTATAATAATTATAAATAAATATTGAC ATTTTTCTTGTCAAATGTTATCATTGTTTTG | promotor variant with SEQ ID NO. 4 and SEQ ID NO. 33 |
| SEQ ID NO. 63 | ATTCAGCATTTATCATGATCAAATCAACGATAATA AATTTTTCTTTATAATAATTATAAATAAATATTGAC ATTTTTCTTGTCAAATGTTATAATTGTTTTG | promotor variant with SEQ ID NO. 4 and SEQ ID NO. 20 and SEQ ID NO. 33 |

-continued

| SEQ ID NO. | sequence | comment |
|---|---|---|
| SEQ ID NO. 64 | ATTCAGCATTTATCATGATCAAATCAACGATAATA AATTTTTCTTTATAATAATTATAAATAAATATTGTT TTTTGTTTTGAGAAATGTTATCATTGTTTTG | promotor variant with SEQ ID NO. 5 |
| SEQ ID NO. 65 | ATTCAGCATTTATCATGATCAAATCAACGATAATA AATTTTTCTTTATAATAATTATAAATAAATATTGTT TTTTGTTTTGAGAAATGTTATAATTGTTTTG | promotor variant with SEQ ID NO. 5 and SEQ ID NO. 20 |
| SEQ ID NO. 66 | ATTCAGCATTTATCATGATCAAATCAACGATAATA AATTTTTCTTTATAATAATTATAAATAAATATTGAC ATTTGTTTTGAGAAATGTTATCATTGTTTTG | promotor variant with SEQ ID NO. 5 and SEQ ID NO. 33 |
| SEQ ID NO. 67 | ATTCAGCATTTATCATGATCAAATCAACGATAATA AATTTTTCTTTATAATAATTATAAATAAATATTGAC ATTTGTTTTGAGAAATGTTATAATTGTTTTG | promotor variant with SEQ ID NO. 5 and SEQ ID NO. 20 and SEQ ID NO. 33 |
| SEQ ID NO. 68 | ATTCAGCATTTATCATGATCAAATCAACGATAATA AATTTTTCTTTATAATAATTATAAATAAATATTGTT TTTTCTTGAGAAAATGTTATCATTGTTTTG | promotor variant with SEQ ID NO. 6 |
| SEQ ID NO. 69 | ATTCAGCATTTATCATGATCAAATCAACGATAATA AATTTTTCTTTATAATAATTATAAATAAATATTGTT TTTTCTTGAGAAAATGTTATAATTGTTTTG | promotor variant with SEQ ID NO. 6 and SEQ ID NO. 20 |
| SEQ ID NO. 70 | ATTCAGCATTTATCATGATCAAATCAACGATAATA AATTTTTCTTTATAATAATTATAAATAAATATTGAC ATTTTCTTGAGAAAATGTTATCATTGTTTTG | promotor variant with SEQ ID NO. 6 and SEQ ID NO. 33 |
| SEQ ID NO. 71 | ATTCAGCATTTATCATGATCAAATCAACGATAATA AATTTTTCTTTATAATAATTATAAATAAATATTGAC ATTTTCTTGAGAAAATGTTATAATTGTTTTG | promotor variant with SEQ ID NO. 6 and SEQ ID NO. 20 and SEQ ID NO. 33 |
| SEQ ID NO. 72 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTTCTTGAGAAA TGTTATCATTGTTTTGTAATTAAAATTTACGCGAG GTGATCCTTTG | bidirectional promotor variant |
| SEQ ID NO. 73 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTTCTTGAGAAA TGTTATAATTGTTTTGTAATTAAAATTTACGCGAG GTGATCCTTTG | bidirectional promotor variant with SEQ ID NO. 20 |
| SEQ ID NO. 74 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTCTTGAGAA ATGTTATCATTGTTTTGTAATTAAAATTTACGCGA GGTGATCCTTTG | bidirectional promotor variant with SEQ ID NO. 33 |
| SEQ ID NO. 75 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTCTTGAGAA ATGTTATAATTGTTTTGTAATTAAAATTTACGCGA GGTGATCCTTTG | bidirectional promotor variant with SEQ ID NO. 20 and SEQ ID NO. 33 |
| SEQ ID NO. 76 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTTCTTGTCAAA TGTTATCATTGTTTTGTAATTAAAATTTACGCGAG GTGATCCTTTG | bidirectional promotor variant with SEQ ID NO. 4 |
| SEQ ID NO. 77 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTTCTTGTCAAA TGTTATAATTGTTTTGTAATTAAAATTTACGCGAG GTGATCCTTTG | bidirectional promotor variant with SEQ ID NO. 4 and SEQ ID NO. 20 |

-continued

| SEQ ID NO. | sequence | comment |
|---|---|---|
| SEQ ID NO. 78 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTTCTTGTCAA ATGTTATCATTGTTTTGTAATTAAAATTTACGCGA GGTGATCCTTTG | bidirectional promotor variant with SEQ ID NO. 4 and SEQ ID NO. 33 |
| SEQ ID NO. 79 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTTCTTGTCAA ATGTTATAATTGTTTTGTAATTAAAATTTACGCGA GGTGATCCTTTG | bidirectional promotor variant with SEQ ID NO. 4 and SEQ ID NO. 20 and SEQ ID NO. 33 |
| SEQ ID NO. 80 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTGTTTTGAGAAAA TGTTATCATTGTTTTGTAATTAAAATTTACGCGAG GTGATCCTTTG | bidirectional promotor variant with SEQ ID NO. 5 |
| SEQ ID NO. 81 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTGTTTTGAGAAA TGTTATAATTGTTTTGTAATTAAAATTTACGCGAG GTGATCCTTTG | bidirectional promotor variant with SEQ ID NO. 5 and SEQ ID NO. 20 |
| SEQ ID NO. 82 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTGTTTTGAGAA ATGTTATCATTGTTTTGTAATTAAAATTTACGCGA GGTGATCCTTTG | bidirectional promotor variant with SEQ ID NO. 5 and SEQ ID NO. 33 |
| SEQ ID NO. 83 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTGTTTTGAGAA ATGTTATAATTGTTTTGTAATTAAAATTTACGCGA GGTGATCCTTTG | bidirectional promotor variant with SEQ ID NO. 5 and SEQ ID NO. 20 and SEQ ID NO. 33 |
| SEQ ID NO. 84 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTCTTGAGAAAA TGTTATCATTGTTTTGTAATTAAAATTTACGCGAG GTGATCCTTTG | bidirectional promotor variant with SEQ ID NO. 6 |
| SEQ ID NO. 85 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGTTTTTTCTTGAGAAAA TGTTATAATTGTTTTGTAATTAAAATTTACGCGAG GTGATCCTTTG | bidirectional promotor variant with SEQ ID NO. 6 and SEQ ID NO. 20 |
| SEQ ID NO. 86 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTCTTGAGAAA ATGTTATCATTGTTTTGTAATTAAAATTTACGCGA GGTGATCCTTTG | bidirectional pronnotor variant with SEQ ID NO. 6 and SEQ ID NO. 33 |
| SEQ ID NO. 87 | TCTTCTTCCTCCTTTATTTGTAATTAACAATAATTT ATCCCAATCCAGAAAAGTTATTCAGCATTTATCA TGATCAAATCAACGATAATAAATTTTTCTTTATAA TAATTATAAATAAATATTGACATTTTCTTGAGAAA ATGTTATAATTGTTTTGTAATTAAAATTTACGCGA GGTGATCCTTTG | bidirectional pronnotor variant with SEQ ID NO. 6 and SEQ ID NO. 20 and SEQ ID NO. 33 |
| SEQ ID NO. 88 | TGTTTTGTAATTAAAATTTACGCGAGGTGATCCTT TG | wt downstream box |
| SEQ ID NO. 89 | TTAGTTGTACTTAACTTTCACTCCTATGAGGTGAT CCTTTG | downstream box |

| SEQ ID NO. | sequence | comment |
|---|---|---|
| SEQ ID NO. 90 | TATTTTGTAATGAAATTTAACGCGAGGTGATCCTTTA | downstream box |
| SEQ ID NO. 91 | TTTTTGGTGTAATTAAAATTTACGCGAGGTGATCCTTTG | downstream box |
| SEQ ID NO. 92 | TGTTTTGTAATTTAAATTTACGCGAGGTGATCCTTTG | downstream box |
| SEQ ID NO. 93 | TTTTTAGTGTAATTAAAATTTACGCGAGGTGATCCTTTG | downstream box |
| SEQ ID NO. 94 | GTTTTGAAATTAAAATTTACGCGAGGTGATCCTTTG | downstream box |
| SEQ ID NO. 95 | TTTTTTTTAATTAAAATTTACGCGAGGTGATCCTTTG | downstream box |
| SEQ ID NO. 96 | TGTTTTATAATTAAAATTTACGCGAGGTGATCCTTTG | downstream box |
| SEQ ID NO. 97 | TTTTTTTAATTAAAATTTACGCGAGGTGATCCTTTG | downstream box |
| SEQ ID NO. 98 | GGTGTTGTAATTAAAATTTACGCGAGGTGATCCTTTG | downstream box |
| SEQ ID NO. 99 | TGGATTATAATTAAAATTTAACGCGAGGTGATCCTTTG | downstream box |

The invention is hereinafter further described by way of examples; the examples are provided for illustrative purposes only and are not intended to limit the invention or the scope of the claims.

EXAMPLES

Example 1

Figure 1:
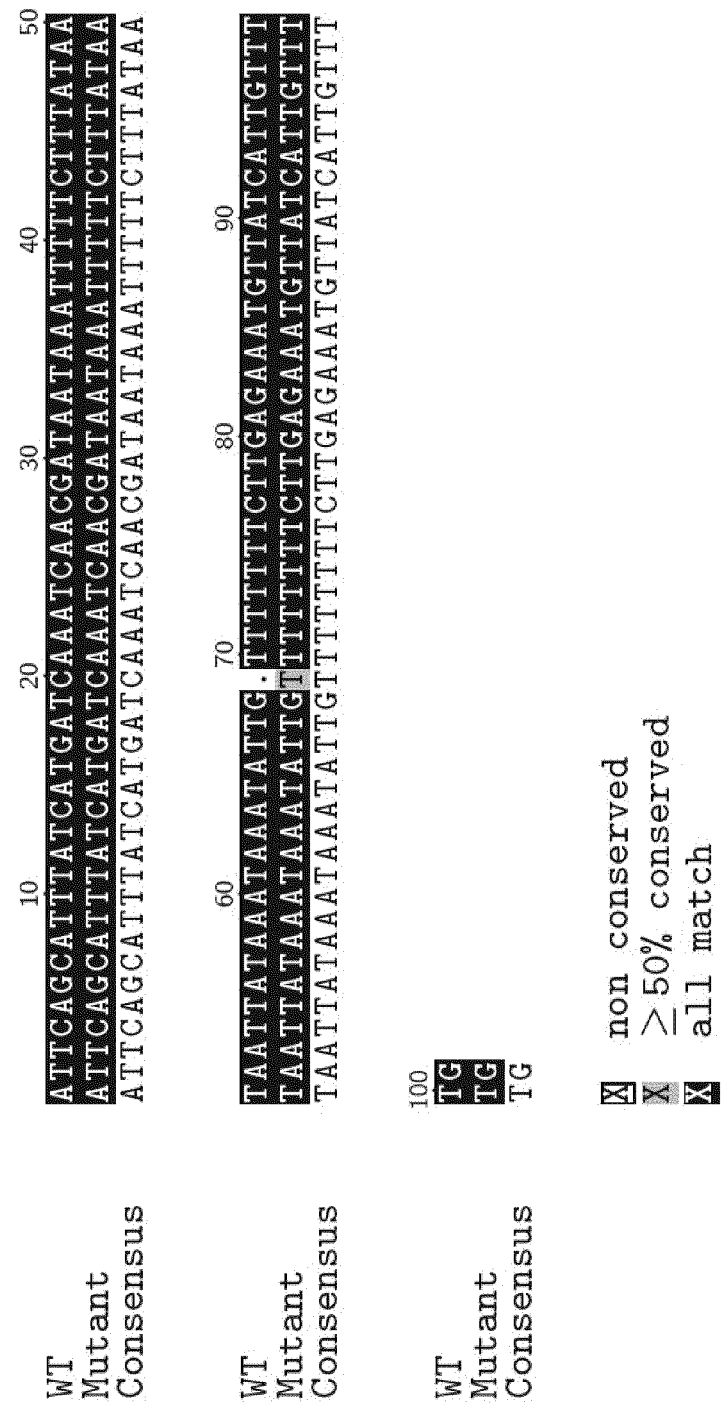
FIG. 1 shows an alignment of the wild-type KatA promoter of *Bacillus licheniformis* to a preferred promoter of the present invention.

Comparison of sequences of a wild-type *Bacillus licheniformis* promoter and of a preferred promoter according to the present invention FIG. 1 depicts an alignment of the wild-type *Bacillus licheniformis* promoter (SEQ ID NO. 1) and the promoter according to SEQ ID NO. 56. The alignment was performed according to the Needleman-Wunsch algorithm with a gap opening penalty of 16 and a gap extension penalty of 4. The sequences differ by insertion of one thymidine in the linker section (compare also FIG. 4).

Example 2

Comparison of KatA and KatX catalase expression in *Bacillus licheniformis* for a wild-type strain and a corresponding strain comprising the promoter according to the present invention of example 1

Fermentation Conditions for Cultivation of *Bacillus licheniformis* Wild-Type and Mutant Strain:

The fermentation processes were conducted in a baffled stirred tank reactor (STR, Dasgip) with pH, pO2 and temperature probes in a medium with glucose as main carbon source and complex compounds. The concentration of O2 and CO2 were monitored by gas analyses. For the cultivations, the fedbatch mode was chosen with a start working volume of 1 L. As bioreactors, 2 L glass vessels were used with 3 rushton turbines with 6 blades.

Medium:

Medium preparation and sterilization for seed and main culture medium took place in the shake flask and bioreactor, respectively. PPG2000 was used in all cultivations as antifoam agent.

The medium contained 30 g/L glucose, 120 g/L complex plant protein, 7.7 g/L KH2PO4, 2.8 g/L (NH4)2SO4, 0.09 g/L Mn(II)SO4*H2O, 0.05 g/L Fe(II)SO4*7H2O, 0.3 g/L CaCl2*2 H2O, 1.4 mL 7 L PPG2000, 0.025 g/L Kanamycin. pH was adjusted to pH 8. The medium was sterilized in the bioreactor under stirred conditions (600 rpm) for 60 min at 123° C.

Seed Culture:

Seed culture were prepared in shake flasks with the same medium as batch cultivation during a 16 h process (39° C., pH 7.5, 200 rpm). Samples were taken regularly and pH, OD, sugars and organic acids (HPLC) as well as protease activity were measured. The shake flasks were inoculated from a fresh LB plate and transferred to the main culture at the end of the exponential phase after 16 h.

Main Culture:

For inoculation 2.7% of the starting working volume was used. The main cultivation was conducted at 39° C., with 30 g/L start glucose concentration and pO2 dependent stirred cascade from 350-1400 rpm and an aeration rate of 1.46 vvm.

Sampling and Total RNA Isolation:

During fermentation 10 ml samples were withdrawn and mixed in a 1:1 ratio with RNAlater Solution (Life Technologies) and immediately placed on dry ice. Samples were carefully thawed on ice and cells pelleted by centrifugation. Total RNA was isolated from cells using the peqGOLD Bacterial RNA Kit (peqlab) following the manufacturers protocol. RNA concentrations were determined measuring the absorbance at 260 nM following dilution to a concentration of 100 ng/μl. RNA samples were stored at −80° C.

Reverse Transcription

Reverse Transcription was performed with 250 ng total RNA with random hexamer oligonucleotides with the GoScript Reverse Transcription System (A5000) (Promega) according to the manufacturers protocol. The reaction is performed in an ABI Genamp PCR System 9700-Cycler.

qPCR:

Quantitative PCR (qPCR) was performed with LightCycler480 II (Roche) and the GoTaq® qPCR Master Mix (A6001-Promega) with 20 µL PCR-reaction volume and 10 pmol oligonucleotides each. SYBR Green was excited in the FAM/SYBR channel at 470 nm and the fluorescence detected at 510 nm.

| Cycling Program | |
| --- | --- |
| 5 min 95° C. | |
| 0:10 min 95° C. | |
| 0:20 min 60° C. | x45 |
| 0:20 min 72° C. | |
| 0:10 min 95° C. | |
| 1:00 min 65° C. | melting curve |
| 97° C. ramprate 0.11° C./s | |
| 40° C. eternal | |

Data evaluation was performed with the software package Ideas 2.0 (Roche Version 1.5.1.62). The ct values are determined by the method of '2nd derivate max'. The relative ct values (−dCT) of indicated target genes are calculated as follows:

$$-dCT = -(ct(TARGET) - ct(REF))$$

qPCR Primers

| Target gene | Sequence |
| --- | --- |
| katA_forward | CCGCCTCTTGAGCGAAGA |
| katA_reverse | TGCTTCATCGAACCTACGATATTG |
| katX_forward | TCCTTGTCGCATTGCTTCAG |
| katX_reverse | CCCCGTGCGACCAAAG |
| 16S rRNA_forward | GAGGGTTTCCGCCCTTTAGT |
| 16S rRNA_reverse | CCCAGGCGGAGTGCTTAA |

Figure 2A:
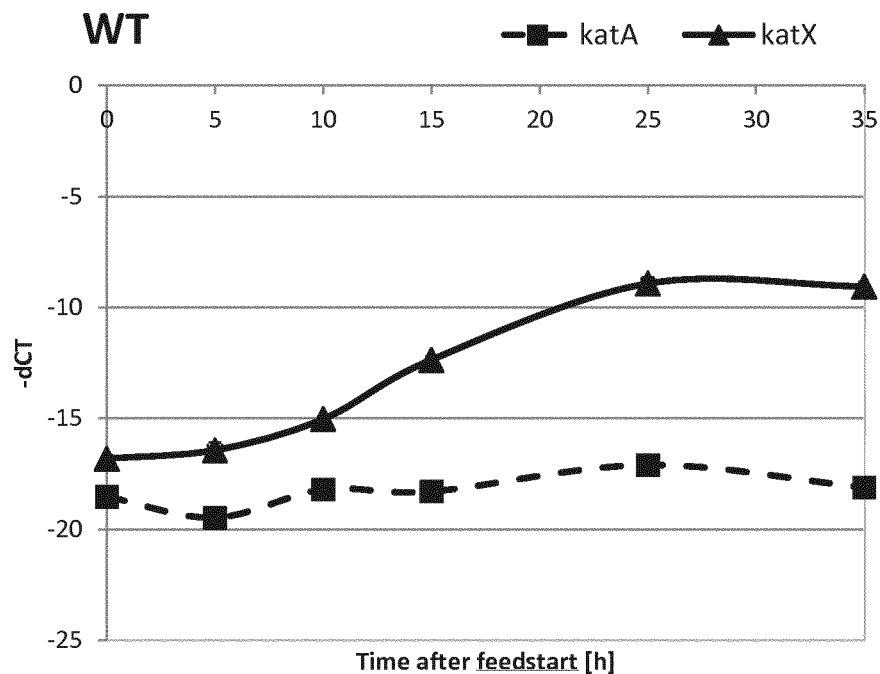
FIG. 2 shows the gene expression characteristics of KatA and KatX genes in *Bacillus licheniformis* with a wild-type promoter and a promoter according to the present invention.
Figure 2B:
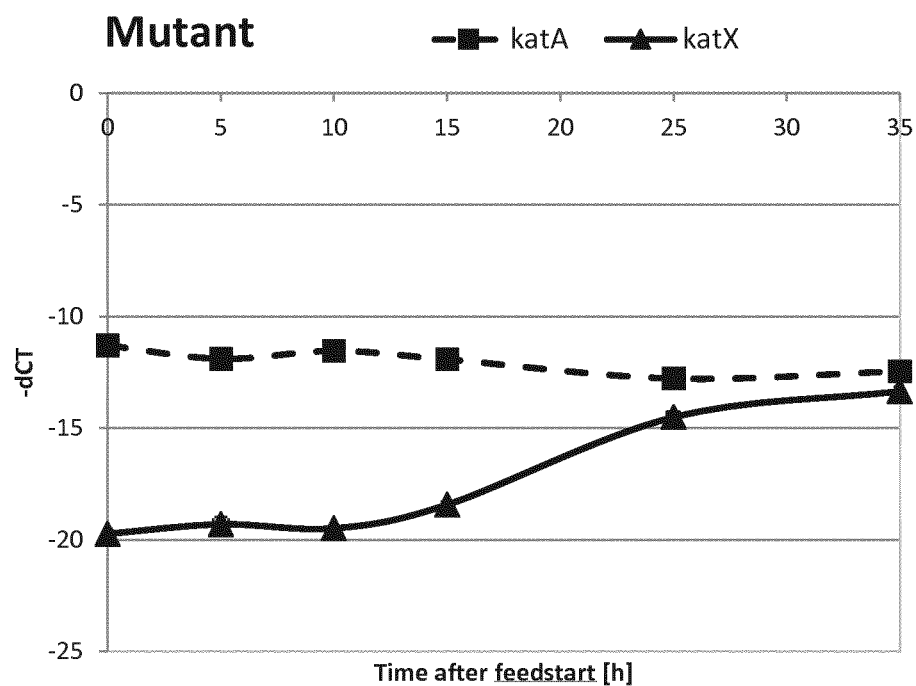

FIG. 2 shows the results of this example. In panel A expression characteristics are given for wild-type *Bacillus licheniformis* and in panel B expression characteristics are given for a recombinant *Bacillus licheniformis* which differs from the wild-type strain of panel A in that the promoter of the KatA gene has been replaced by the promoter sequence of the present invention depicted in FIG. 1. Gene expression is determined by quantitative PCR of mRNA coding for KatA and KatX proteins, respectively. Panel B proves that the preferred promoter according to the present invention leads to a constitutively increased expression of the KatA gene without unduely reducing the expression of the KatX gene, and also that expression of the KatX gene is still induced during fermentation. Example 3: Comparison of total catalase activity *Bacillus licheniformis* for a wild-type strain and a corresponding strain comprising the promoter according to the present invention of example 1 1 ml samples were withdrawn from cultivation following centrifugation. Cells were resuspended in assay buffer with 1 mM PMSF (see below) and disrupted using Ribolyser (MP Biomedicals). After centrifugation, supernatant was recovered and used for catalase activity assay.

Catalase activity was assayed by the aminoantipyrine-phenol method. Herefore 10 µL of a catalase containing sample was incubated for 5 min at room temperature with 60 µL 0.86 mM H2O2 dissolved in a 166 mM Phosphate buffer at pH 7. After incubation residual H2O2 was detected spectrophotometrically by adding 30 µL of a mixture containing 50 mM Phenol, 2.6 mM 4-Aminoantipyrine and 90 U/mL horseradish Peroxidase (Sigma 77332) at 520 nM in a microtiter plate reader. For calibration, catalase from bovine liver (Sigma C40) was used, by taking a serial dilution from 500 U/mL to 0.5 U/mL. For normalization purposes the catalase activity was normalized on the total protein concentration measured by the micro-BCA protein determination kit (Pierce).

Figure 3:
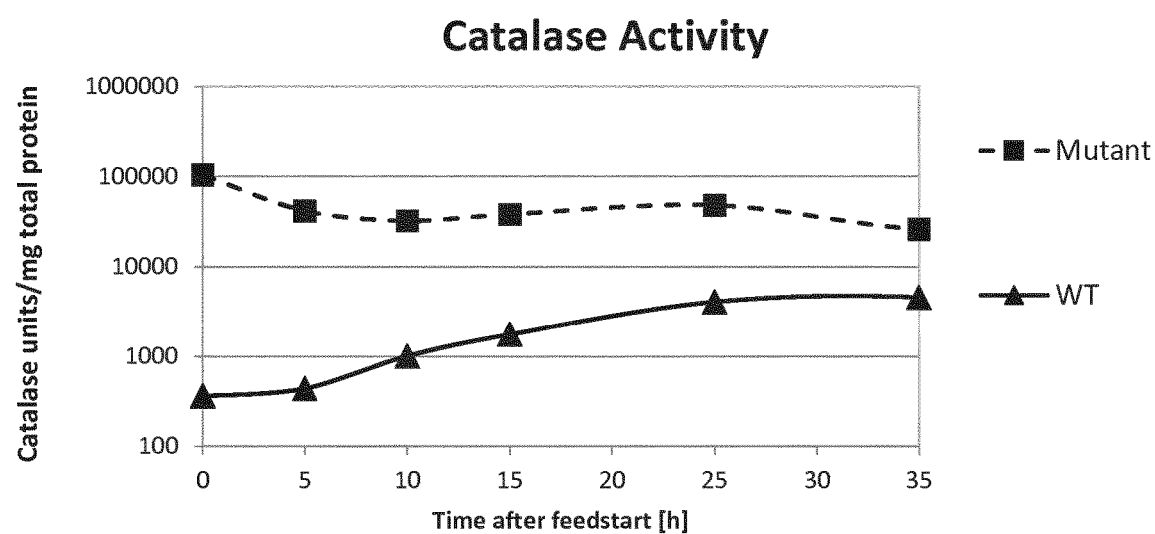
FIG. 3 shows a comparison of total catalase activity in wild-type *Bacillus licheniformis* (labelled "WT") and in *Bacillus licheniformis* wherein the promoter of the KatA gene has been replaced by the preferred promoter according to the present invention depicted in FIG. 1 (labelled "Mutant").

The results of this example are shown in FIG. 3. The figure shows that overall catalase activity is increased at least by a factor of 10 compared to the wild-type strain, and during the first 5 h after fermentation feedstart by a factor of 100.

The invention claimed is:

1. A method of increasing catalase expression or activity in a prokaryotic host cell, comprising the step of introducing into the host cell a nucleic acid comprising a promoter operably linked to a gene coding for a catalase, the promoter comprising a −10 type box and a −35 type box separated from one another by a linker section, wherein each box consists of a respective nucleotide sequence with a respective score obtainable by assigning a value to each nucleotide at each position according to table 1 for the −10 type box:

TABLE 1

| position (5'->3' direction) | A | C | G | T |
| --- | --- | --- | --- | --- |
| 1 | 0 | 0 | 0 | 100 |
| 2 | 0 | 0 | 100 | 0 |
| 3 | 28 | 6 | 30 | 36 |
| 4 | 8 | 5 | 0 | 88 |
| 5 | 94 | 0 | 2 | 5 |
| 6 | 23 | 11 | 6 | 59 |
| 7 | 73 | 5 | 6 | 16 |
| 8 | 63 | 20 | 3 | 14 |
| 9 | 2 | 2 | 2 | 95 | and according to table 2 for the −35 type box:

TABLE 2

| position (5'->3' direction) | A | C | G | T |
|---|---|---|---|---|
| 1 | 2 | 3 | 0 | 95 |
| 2 | 6 | 3 | 2 | 89 |
| 3 | 2 | 8 | 81 | 9 |
| 4 | 63 | 16 | 3 | 19 |
| 5 | 20 | 58 | 5 | 17 |
| 6 | 53 | 8 | 11 | 28 | wherein the score for the −10 type box is at least 497 and for the −35 type box is at least 179,
wherein the linker section has a length of at least 14 nucleotides and an A/T content of at least 57%, and
wherein the nucleotide sequence of the linker section differs from any of SEQ ID NOS: 3 to 18 by insertion of a thymidine before any of nucleotide positions 1 to 5 of these sequences.

2. The method of claim 1, wherein the linker section has a length of at most 18 nucleotides.

3. The method of claim 1, wherein the nucleotide sequence of the −10 type box differs from any of the sequences SEQ ID NO. 19 to 31 by at most 1 nucleotide.

4. The method of claim 1, wherein the nucleotide sequence of the −35 type box differs from any of the sequences SEQ ID NO. 32 to 41 by at most 1 nucleotide.

5. The method of claim 1, wherein an upstream section having a length of 20 nucleotides is located in 5' direction upstream of and adjacent to the −35 type box, wherein the A/T content of the upstream section is at least 70% and the A content of the upstream region is at least 35%.

6. The method of claim 1, wherein the promotor is a bidirectional promoter.

* * * * *

SEQUENCE LISTING

<160> NUMBER OF SEQ ID NOS: 105

<210> SEQ ID NO 1
<211> LENGTH: 101
<212> TYPE: DNA
<213> ORGANISM: Bacillus licheniformis
<220> FEATURE:
<221> NAME/KEY: misc_feature
<223> OTHER INFORMATION: wt promoter

<400> SEQUENCE: 1
attcagcatt tatcatgatc aaatcaacga taataaattt ttctttataa taattataaa      60
taaatattgt tttttcttg agaaatgtta tcattgtttt g      101

<210> SEQ ID NO 2
<211> LENGTH: 186
<212> TYPE: DNA

```
<213> ORGANISM: Bacillus licheniformis
<220> FEATURE:
<221> NAME/KEY: misc_feature
<223> OTHER INFORMATION: wt promoter

<400> SEQUENCE: 2
tcttcttcct cctttatttg taattaacaa taatttatcc caatccagaa aagttattca      60
gcatttatca tgatcaaatc aacgataata aatttttctt tataataatt ataaataaat     120
attgtttttt tcttgagaaa tgttatcatt gttttgtaat taaaatttac gcgaggtgat     180
cctttg                                                                186

<210> SEQ ID NO 3
<211> LENGTH: 13
<212> TYPE: DNA
<213> ORGANISM: Bacillus licheniformis
<220> FEATURE:
<221> NAME/KEY: misc_feature
<223> OTHER INFORMATION: 77% A/T content wt linker

<400> SEQUENCE: 3
ttttcttgag aaa                                                         13

<210> SEQ ID NO 4
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 77% A/T content linker; minus strand comprises
      "TTGACA" -35 type box

<400> SEQUENCE: 4
ttttcttgtc aaa                                                         13

<210> SEQ ID NO 5
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 77% A/T content linker; minus strand comprises
      "TTCTCA" Ka tX -35 type box

<400> SEQUENCE: 5
ttgttttgag aaa                                                         13

<210> SEQ ID NO 6
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 77% A/T content linker; minus strand comprises
      "TTCTCA" Ka tX -35 type box

<400> SEQUENCE: 6
tttcttgaga aaa                                                         13

<210> SEQ ID NO 7
<211> LENGTH: 13
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 77% A/T content linker; minus strand comprises
      "TTGTCA" score 395 -35 type box

<400> SEQUENCE: 7
ttagattgac aaa                                                          13

<210> SEQ ID NO 8
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTCTCA" Ka tX -35 type box

<400> SEQUENCE: 8
ttgcattgag aaa                                                          13

<210> SEQ ID NO 9
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTGTCA" score 395 -35 type box

<400> SEQUENCE: 9
tttgagtgac aaa                                                          13

<210> SEQ ID NO 10
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTGATT" score 373 -35 type box, cf. SEQ ID NO. 36

<400> SEQUENCE: 10
tccaaatcaa aga                                                          13

<210> SEQ ID NO 11
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTCTCA" Ka tX -35 type box

<400> SEQUENCE: 11
ttgagtgaga aaa                                                          13

<210> SEQ ID NO 12
```

```
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTGTCA" score 395 -35 type box

<400> SEQUENCE: 12
ttttcttgac aag                                                         13

<210> SEQ ID NO 13
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 69% A/T content linker; minus strand comprises
      "TTTACA" score 367 -35 type box, cf. SEQ ID NO. 37

<400> SEQUENCE: 13
ttttgtgtaa agg                                                         13

<210> SEQ ID NO 14
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 85% A/T content linker; minus strand comprises
      "TTTTCA" score 323 -35 type box, cf. SEQ ID NO. 38

<400> SEQUENCE: 14
ttttcttgaa aaa                                                         13

<210> SEQ ID NO 15
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 85% A/T content linker; minus strand comprises
      "TTGTAA" score 357 -35 type box

<400> SEQUENCE: 15
ttttctttac aaa                                                         13

<210> SEQ ID NO 16
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 85% A/T content linker; minus strand comprises
      "TTCTCA" Ka tX -35 type box

<400> SEQUENCE: 16
attttttgag aaa                                                         13
```

<210> SEQ ID NO 17
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 85% A/T content linker; minus strand comprises
      "TTCTCA" Ka tX -35 type box

<400> SEQUENCE: 17
tttatgagaa taa                                                       13

<210> SEQ ID NO 18
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 92% A/T content linker; minus strand comprises
      "TTGTTT" Ka tA -35 type box

<400> SEQUENCE: 18 tttttaaac aaa                                                        13

<210> SEQ ID NO 19
<211> LENGTH: 9
<212> TYPE: DNA
<213> ORGANISM: Bacillus licheniformis
<220> FEATURE:
<221> NAME/KEY: misc_feature
<223> OTHER INFORMATION: 640 score KatA wt -10 type box

<400> SEQUENCE: 19 tgttatcat                                                             9

<210> SEQ ID NO 20
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 708 score -10 type box

<400> SEQUENCE: 20 tgttataat                                                             9

<210> SEQ ID NO 21
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 641 score -10 type box

<400> SEQUENCE: 21 tgttatgat                                                             9

<210> SEQ ID NO 22
<211> LENGTH: 9
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<223> OTHER INFORMATION: 632 score -10 type box

<400> SEQUENCE: 22 tgatatcat                                                                 9

<210> SEQ ID NO 23
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 558 score -10 type box

<400> SEQUENCE: 23 tgttattaa                                                                 9

<210> SEQ ID NO 24
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 608 score -10 type box

<400> SEQUENCE: 24 tattataat                                                                 9

<210> SEQ ID NO 25
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 600 score -10 type box

<400> SEQUENCE: 25 taatataat                                                                 9

<210> SEQ ID NO 26
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 572 score -10 type box

<400> SEQUENCE: 26 tattaaaat                                                                 9

<210> SEQ ID NO 27
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<223> OTHER INFORMATION: 492 score -10 type box

<400> SEQUENCE: 27 tattatgtt                                                                 9

<210> SEQ ID NO 28
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 508 score -10 type box

<400> SEQUENCE: 28 atttataat                                                                 9

<210> SEQ ID NO 29
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 472 score -10 type box

<400> SEQUENCE: 29 atttaaaat                                                                 9

<210> SEQ ID NO 30
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 502 score -10 type box

<400> SEQUENCE: 30 ttttatttt                                                                 9

<210> SEQ ID NO 31
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 462 score -10 type box

<400> SEQUENCE: 31 tttttttat                                                                 9

<210> SEQ ID NO 32
<211> LENGTH: 6
<212> TYPE: DNA
<213> ORGANISM: Bacillus licheniformis
<220> FEATURE:
<221> NAME/KEY: misc_feature
<223> OTHER INFORMATION: 640 score KatA wt -10 type box

<400> SEQUENCE: 32 ttgttt                                                                    6
```

```
<210> SEQ ID NO 33
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 439 score -35 type box

<400> SEQUENCE: 33 ttgaca                                                                       6

<210> SEQ ID NO 34
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 414 score -35 type box

<400> SEQUENCE: 34 ttgact                                                                       6

<210> SEQ ID NO 35
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 401 score -35 type box

<400> SEQUENCE: 35 ttgaaa                                                                       6

<210> SEQ ID NO 36
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 373 score -35 type box

<400> SEQUENCE: 36 ttgatt                                                                       6

<210> SEQ ID NO 37
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 367 score -35 type box

<400> SEQUENCE: 37 tttaca                                                                       6

<210> SEQ ID NO 38
<211> LENGTH: 6
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 323 score -35 type box

<400> SEQUENCE: 38 ttttca                                                                          6

<210> SEQ ID NO 39
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 322 score -35 type box

<400> SEQUENCE: 39 ttctca                                                                          6

<210> SEQ ID NO 40
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 300 score -35 type box

<400> SEQUENCE: 40 ttcatt                                                                          6

<210> SEQ ID NO 41
<211> LENGTH: 6
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 281 score -35 type box

<400> SEQUENCE: 41 ttctta                                                                          6

<210> SEQ ID NO 42
<211> LENGTH: 20
<212> TYPE: DNA
<213> ORGANISM: Bacillus licheniformis
<220> FEATURE:
<221> NAME/KEY: misc_feature
<223> OTHER INFORMATION: wt upstream box

<400> SEQUENCE: 42
ataataatta taaataaata                                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box
```

-continued

<400> SEQUENCE: 43
tataataatt ataaataaat                                        20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 44
ttataataat tataaataaa                                        20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 45
tttataataa tttataaataa                                       20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 46
ctttataata attataaata                                        20

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 47
tctttataat aattataaat                                        20

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 48
ataataatta taaataaatc                                        20

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 49
tataataatt ataaataaac                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 50
ttataataat tataaataac                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 51
tttataataa ttataaatac                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 52
ctttataata attataaatc                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 53
tctttataat aattataaac                                              20

<210> SEQ ID NO 54
<211> LENGTH: 20

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 54
cataataatt ataaatagac                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: upstream box

<400> SEQUENCE: 55
tcataataat tataaatgac                                                    20

<210> SEQ ID NO 56
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant

<400> SEQUENCE: 56
attcagcatt tatcatgatc aaatcaacga taataaattt ttctttataa taattataaa        60
taaatattgt tttttttctt gagaaatgtt atcattgttt tg                          102

<210> SEQ ID NO 57
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 20

<400> SEQUENCE: 57
attcagcatt tatcatgatc aaatcaacga taataaattt ttctttataa taattataaa        60
taaatattgt tttttttctt gagaaatgtt ataattgttt tg                          102

<210> SEQ ID NO 58
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 33

<400> SEQUENCE: 58
attcagcatt tatcatgatc aaatcaacga taataaattt ttctttataa taattataaa        60
taaatattga catttttctt gagaaatgtt atcattgttt tg                          102
```

```
<210> SEQ ID NO 59
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 20 and SEQ ID
      NO. 33

<400> SEQUENCE: 59
attcagcatt tatcatgatc aaatcaacga taataaattt ttctttataa taattataaa      60
taaatattga catttttctt gagaaatgtt ataattgttt tg                        102

<210> SEQ ID NO 60
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 4

<400> SEQUENCE: 60
attcagcatt tatcatgatc aaatcaacga taataaattt ttctttataa taattataaa      60
taaatattgt ttttttctt gtcaaatgtt atcattgttt tg                         102

<210> SEQ ID NO 61
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 4 and SEQ ID
      NO. 20

<400> SEQUENCE: 61
attcagcatt tatcatgatc aaatcaacga taataaattt ttctttataa taattataaa      60
taaatattgt ttttttctt gtcaaatgtt ataattgttt tg                         102

<210> SEQ ID NO 62
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 4 and SEQ ID
      NO. 33

<400> SEQUENCE: 62
attcagcatt tatcatgatc aaatcaacga taataaattt ttctttataa taattataaa      60
taaatattga catttttctt gtcaaatgtt atcattgttt tg                        102

<210> SEQ ID NO 63
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

<223> OTHER INFORMATION: promotor variant with SEQ ID NO. 4 and SEQ ID
      NO. 20 and SEQ ID NO. 33

<400> SEQUENCE: 63
attcagcatt tatcatgatc aaatcaacga taataaattt ttctttataa taattataaa    60
taaatattga cattttctt gtcaaatgtt ataattgttt tg                      102

<210> SEQ ID NO 64
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 5

<400> SEQUENCE: 64
attcagcatt tatcatgatc aaatcaacga taataaattt ttctttataa taattataaa    60
taaatattgt ttttgttttt gagaaatgtt atcattgttt tg                      102

<210> SEQ ID NO 65
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 5 and SEQ ID
      NO. 20

<400> SEQUENCE: 65
attcagcatt tatcatgatc aaatcaacga taataaattt ttctttataa taattataaa    60
taaatattgt ttttgttttt gagaaatgtt ataattgttt tg                      102

<210> SEQ ID NO 66
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 5 and SEQ ID
      NO. 33

<400> SEQUENCE: 66
attcagcatt tatcatgatc aaatcaacga taataaattt ttctttataa taattataaa    60
taaatattga catttgtttt gagaaatgtt atcattgttt tg                      102

<210> SEQ ID NO 67
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 5 and SEQ ID
      NO. 20 and SEQ ID NO. 33

<400> SEQUENCE: 67
attcagcatt tatcatgatc aaatcaacga taataaattt ttctttataa taattataaa    60
taaatattga catttgtttt gagaaatgtt ataattgttt tg                      102

<210> SEQ ID NO 68
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 6

<400> SEQUENCE: 68
attcagcatt tatcatgatc aaatcaacga taataaattt ttctttataa taattataaa      60
taaatattgt tttttcttg agaaaatgtt atcattgttt tg                         102

<210> SEQ ID NO 69
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 6 and SEQ ID
      NO. 20

<400> SEQUENCE: 69
attcagcatt tatcatgatc aaatcaacga taataaattt ttctttataa taattataaa      60
taaatattgt tttttcttg agaaaatgtt ataattgttt tg                         102

<210> SEQ ID NO 70
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 6 and SEQ ID
      NO. 33

<400> SEQUENCE: 70
attcagcatt tatcatgatc aaatcaacga taataaattt ttctttataa taattataaa      60
taaatattga cattttcttg agaaaatgtt atcattgttt tg                        102

<210> SEQ ID NO 71
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: promotor variant with SEQ ID NO. 6 and SEQ ID
      NO. 20 and SEQ ID NO. 33

<400> SEQUENCE: 71
attcagcatt tatcatgatc aaatcaacga taataaattt ttctttataa taattataaa      60
taaatattga cattttcttg agaaaatgtt ataattgttt tg                        102

<210> SEQ ID NO 72
<211> LENGTH: 187
<212> TYPE: DNA
<213> ORGANISM: Artificial Sequence
<220> FEATURE:
<223> OTHER INFORMATION: Synthetic Polynucleotide

```
<220> FEATURE:
<221> NAME/KEY: misc_feature
<223> OTHER INFORMATION: bidirectional promotor variant

<400> SEQUENCE: 72
tcttcttcct cctttatttg taattaacaa taatttatcc caatccagaa aagttattca        60
gcatttatca tgatcaaatc aacgataata aattttctt tataataatt ataaataaat        120 attgttttt tcttgagaa atgttatcat tgttttgtaa ttaaaattta cgcgaggtga        180
tcctttg                                                                 187

<210> SEQ ID NO 73
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      20

<400> SEQUENCE: 73
tcttcttcct cctttatttg taattaacaa taatttatcc caatccagaa aagttattca        60
gcatttatca tgatcaaatc aacgataata aattttctt tataataatt ataaataaat        120 attgttttt tcttgagaa atgttataat tgttttgtaa ttaaaattta cgcgaggtga        180
tcctttg                                                                 187

<210> SEQ ID NO 74
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      33

<400> SEQUENCE: 74
tcttcttcct cctttatttg taattaacaa taatttatcc caatccagaa aagttattca        60
gcatttatca tgatcaaatc aacgataata aattttctt tataataatt ataaataaat        120
attgacattt tcttgagaa atgttatcat tgttttgtaa ttaaaattta cgcgaggtga        180
tcctttg                                                                 187

<210> SEQ ID NO 75
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      20 and SEQ ID NO. 33

<400> SEQUENCE: 75
tcttcttcct cctttatttg taattaacaa taatttatcc caatccagaa aagttattca        60
gcatttatca tgatcaaatc aacgataata aattttctt tataataatt ataaataaat        120
attgacattt tcttgagaa atgttataat tgttttgtaa ttaaaattta cgcgaggtga        180
tcctttg                                                                 187
```

```
<210> SEQ ID NO 76
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      4

<400> SEQUENCE: 76
tcttcttcct cctttatttg taattaacaa taatttatcc caatccagaa aagttattca      60
gcatttatca tgatcaaatc aacgataata aattttctt tataataatt ataaataaat      120 attgttttt ttcttgtcaa atgttatcat tgttttgtaa ttaaaattta cgcgaggtga      180
tcctttg                                                               187

<210> SEQ ID NO 77
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      4 and SEQ ID NO. 20

<400> SEQUENCE: 77
tcttcttcct cctttatttg taattaacaa taatttatcc caatccagaa aagttattca      60
gcatttatca tgatcaaatc aacgataata aattttctt tataataatt ataaataaat      120 attgttttt ttcttgtcaa atgttataat tgttttgtaa ttaaaattta cgcgaggtga      180
tcctttg                                                               187

<210> SEQ ID NO 78
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      4 and SEQ ID NO. 33

<400> SEQUENCE: 78
tcttcttcct cctttatttg taattaacaa taatttatcc caatccagaa aagttattca      60
gcatttatca tgatcaaatc aacgataata aattttctt tataataatt ataaataaat      120
attgacattt ttcttgtcaa atgttatcat tgttttgtaa ttaaaattta cgcgaggtga      180
tcctttg                                                               187

<210> SEQ ID NO 79
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      4 and SEQ ID NO. 20 and SEQ ID NO. 33
```

<400> SEQUENCE: 79
tcttcttcct cctttatttg taattaacaa taatttatcc caatccagaa aagttattca    60
gcatttatca tgatcaaatc aacgataata aatttttctt tataataatt ataaataaat   120
attgacattt ttcttgtcaa atgttataat tgttttgtaa ttaaaattta cgcgaggtga   180
tcctttg                                                             187

<210> SEQ ID NO 80
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      5

<400> SEQUENCE: 80
tcttcttcct cctttatttg taattaacaa taatttatcc caatccagaa aagttattca    60
gcatttatca tgatcaaatc aacgataata aatttttctt tataataatt ataaataaat   120 attgttttt gttttgagaa atgttatcat tgttttgtaa ttaaaattta cgcgaggtga   180
tcctttg                                                             187

<210> SEQ ID NO 81
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      5 and SEQ ID NO. 20

<400> SEQUENCE: 81
tcttcttcct cctttatttg taattaacaa taatttatcc caatccagaa aagttattca    60
gcatttatca tgatcaaatc aacgataata aatttttctt tataataatt ataaataaat   120 attgttttt gttttgagaa atgttataat tgttttgtaa ttaaaattta cgcgaggtga   180
tcctttg                                                             187

<210> SEQ ID NO 82
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      5 and SEQ ID NO. 33

<400> SEQUENCE: 82
tcttcttcct cctttatttg taattaacaa taatttatcc caatccagaa aagttattca    60
gcatttatca tgatcaaatc aacgataata aatttttctt tataataatt ataaataaat   120
attgacattt gttttgagaa atgttatcat tgttttgtaa ttaaaattta cgcgaggtga   180
tcctttg                                                             187

<210> SEQ ID NO 83
<211> LENGTH: 187

-continued

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      5 and SEQ ID NO. 20 and SEQ ID NO. 33

<400> SEQUENCE: 83
tcttcttcct cctttatttg taattaacaa taatttatcc caatccagaa aagttattca    60
gcatttatca tgatcaaatc aacgataata aattttcctt tataataatt ataaataaat   120
attgacattt gttttgagaa atgttataat tgttttgtaa ttaaaattta cgcgaggtga   180
tcctttg                                                              187

<210> SEQ ID NO 84
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      6

<400> SEQUENCE: 84
tcttcttcct cctttatttg taattaacaa taatttatcc caatccagaa aagttattca    60
gcatttatca tgatcaaatc aacgataata aattttcctt tataataatt ataaataaat   120
attgtttttt tcttgagaaa atgttatcat tgttttgtaa ttaaaattta cgcgaggtga   180
tcctttg                                                              187

<210> SEQ ID NO 85
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      6 and SEQ ID NO. 20

<400> SEQUENCE: 85
tcttcttcct cctttatttg taattaacaa taatttatcc caatccagaa aagttattca    60
gcatttatca tgatcaaatc aacgataata aattttcctt tataataatt ataaataaat   120
attgtttttt tcttgagaaa atgttataat tgttttgtaa ttaaaattta cgcgaggtga   180
tcctttg                                                              187

<210> SEQ ID NO 86
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      6 and SEQ ID NO. 33

<400> SEQUENCE: 86
tcttcttcct cctttatttg taattaacaa taatttatcc caatccagaa aagttattca    60
```
gcatttatca tgatcaaatc aacgataata aattttctt tataataatt ataaataaat    120
attgacattt tcttgagaaa atgttatcat tgttttgtaa ttaaaattta cgcgaggtga    180
tcctttg                                                              187

<210> SEQ ID NO 87
<211> LENGTH: 187
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: bidirectional promotor variant with SEQ ID NO.
      6 and SEQ ID NO. 20 and SEQ ID NO. 33

<400> SEQUENCE: 87
tcttcttcct cctttatttg taattaacaa taatttatcc caatccagaa aagttattca    60
gcatttatca tgatcaaatc aacgataata aattttctt tataataatt ataaataaat    120
attgacattt tcttgagaaa atgttataat tgttttgtaa ttaaaattta cgcgaggtga    180
tcctttg                                                              187

<210> SEQ ID NO 88
<211> LENGTH: 37
<212> TYPE: DNA
<213> ORGANISM: Bacillus licheniformis
<220> FEATURE:
<221> NAME/KEY: misc_feature
<223> OTHER INFORMATION: wt downstream box

<400> SEQUENCE: 88
tgttttgtaa ttaaaattta cgcgaggtga tcctttg                             37

<210> SEQ ID NO 89
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 89
ttagttgtac ttaactttca ctcctatgag gtgatccttt g                        41

<210> SEQ ID NO 90
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 90
tattttgtaa tgaaatttaa cgcgaggtga tccttta                             37

<210> SEQ ID NO 91
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:

<221> NAME/KEY: misc_feature
<223> OTHER INFORMATION: downstream box

<400> SEQUENCE: 91
tttttggtgt aattaaaatt tacgcgaggt gatcctttg               39

<210> SEQ ID NO 92
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 92
tgttttgtaa tttaaattta cgcgaggtga tcctttg                 37

<210> SEQ ID NO 93
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 93
tttttagtgt aattaaaatt tacgcgaggt gatcctttg               39

<210> SEQ ID NO 94
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 94
gttttgaaat taaaatttac gcgaggtgat cctttg                  36

<210> SEQ ID NO 95
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 95 tttttttaa ttaaaattta cgcgaggtga tcctttg                  37

<210> SEQ ID NO 96
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 96
tgttttataa ttaaaattta cgcgaggtga tcctttg                                 37

<210> SEQ ID NO 97
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 97
tttttttaat taaaatttac gcgaggtgat cctttg                                  36

<210> SEQ ID NO 98
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 98
ggtgttgtaa ttaaaattta cgcgaggtga tcctttg                                 37

<210> SEQ ID NO 99
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: downstream box

<400> SEQUENCE: 99
tggattataa ttaaaattta acgcgaggtg atcctttg                                38

<210> SEQ ID NO 100
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: katA_forward

<400> SEQUENCE: 100
ccgcctcttg agcgaaga                                                      18

<210> SEQ ID NO 101
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: katA_reverse

<400> SEQUENCE: 101
tgcttcatcg aacctacgat attg                                               24

```
<210> SEQ ID NO 102
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: katX_forward

<400> SEQUENCE: 102
tccttgtcgc attgcttcag                                         20

<210> SEQ ID NO 103
<211> LENGTH: 16
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: katX_reverse

<400> SEQUENCE: 103
ccccgtgcga ccaaag                                             16

<210> SEQ ID NO 104
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: 16S rRNA_forward

<400> SEQUENCE: 104
gagggtttcc gcccttagt                                          20

<210> SEQ ID NO 105
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer: 16S rRNA _reverse

<400> SEQUENCE: 105
cccaggcgga gtgcttaa                                           18
```